(12) United States Patent
West et al.

(10) Patent No.: US 7,651,697 B2
(45) Date of Patent: *Jan. 26, 2010

(54) NITRIC OXIDE-PRODUCING HYDROGEL MATERIALS

(75) Inventors: Jennifer L. West, Pearland, TX (US); Kristyn Simcha Masters, Northglenn, CO (US)

(73) Assignee: Rice University, Houston, TX (US)

( * ) Notice: Subject to any disclaimer, the term of this patent is extended or adjusted under 35 U.S.C. 154(b) by 348 days.

This patent is subject to a terminal disclaimer.

(21) Appl. No.: 11/281,242

(22) Filed: Nov. 17, 2005

(65) Prior Publication Data

US 2006/0153795 A1 Jul. 13, 2006

Related U.S. Application Data

(60) Division of application No. 10/129,418, filed as application No. PCT/US01/27414 on Sep. 4, 2001, now Pat. No. 7,052,711, which is a continuation-in-part of application No. 09/653,406, filed on Sep. 1, 2000, now Pat. No. 7,279,176.

(60) Provisional application No. 60/152,054, filed on Sep. 2, 1999.

(51) Int. Cl.
    *A61F 2/02* (2006.01)
(52) U.S. Cl. .................................................. 424/426
(58) Field of Classification Search ...................... None
    See application file for complete search history.

(56) References Cited

U.S. PATENT DOCUMENTS 4,526,938 A 7/1985 Churchill et al.

(Continued)

FOREIGN PATENT DOCUMENTS

WO  WO 96/15797  5/1996

(Continued)

OTHER PUBLICATIONS

Bohl et al., "Nitric oxide-generating polymers reduce platelet adhesion and smooth muscle cell proliferation", Biomaterials, 2000, 2273-2278, vol. 21.

(Continued)

*Primary Examiner*—Carlos A Azpuru
(74) *Attorney, Agent, or Firm*—Kilpatrick Stockton LLP

(57) ABSTRACT

Hydrogels releasing or producing NO, most preferably polymerizable biodegradable hydrogels capable of releasing physiological amounts of NO for prolonged periods of time, are applied to sites on or in a patient in need of treatment thereof for disorders such as restenosis, thrombosis, asthma, wound healing, arthritis, penile erectile dysfunction or other conditions where NO plays a significant role. The polymeric materials can be formed into films, coatings, or microparticles for application to medical devices, such as stents, vascular grafts and catheters. The polymeric materials can also be applied directly to biological tissues and can be polymerized in situ. The hydrogels are formed of macromers, which preferably include biodegradable regions, and have bound thereto groups that are released in situ to elevate or otherwise modulate NO levels at the site where treatment is needed. The macromers can form a homo or hetero-dispersion or solution, which is polymerized to form a hydrogel material, that in the latter case can be a semi-interpenetrating network or interpenetrating network. Compounds to be released can be physically entrapped, covalently or ionically bound to macromer, or actually form a part of the polymeric material. The hydrogel can be formed by ionic and/or covalent crosslinking. Other active agents, including therapeutic, prophylactic, or diagnostic agents, can also be included within the polymeric material.

8 Claims, 20 Drawing Sheets

U.S. PATENT DOCUMENTS

| | | | |
|---|---|---|---|
| 4,716,203 | A | 12/1987 | Casey et al. |
| 4,741,337 | A | 5/1988 | Smith et al. |
| 4,957,744 | A | 9/1990 | della Valle et al. |
| 4,987,744 | A | 1/1991 | Handley et al. |
| 5,410,016 | A | 4/1995 | Hubbell et al. |
| 5,508,317 | A | 4/1996 | Müller |
| 5,632,981 | A | 5/1997 | Saavedra et al. |
| 5,665,840 | A | 9/1997 | Pöhlmann et al. |
| 5,797,887 | A | 8/1998 | Rosen et al. |
| 5,807,927 | A | 9/1998 | Stockinger et al. |
| 5,849,839 | A | 12/1998 | Hubbell et al. |
| 5,849,841 | A | 12/1998 | Mühlebach et al. |
| 5,879,713 | A | 3/1999 | Roth et al. |
| 5,900,433 | A | 5/1999 | Igo et al. |
| 5,910,316 | A | 6/1999 | Keefer et al. |
| 5,932,674 | A | 8/1999 | Müller |
| 5,939,489 | A | 8/1999 | Müller |
| 5,994,444 | A | 11/1999 | Trescony et al. |
| 6,011,077 | A | 1/2000 | Müller |
| 6,262,206 | B1 | 7/2001 | Nesvadba et al. |
| 6,299,604 | B1 | 10/2001 | Ragheb et al. |
| 7,052,711 | B2 | 5/2006 | West |
| 7,279,176 | B1 * | 10/2007 | West et al. .......... 424/426 |

FOREIGN PATENT DOCUMENTS

| | | |
|---|---|---|
| WO | WO 96/32136 | 10/1996 |
| WO | WO 01/15738 | 3/2001 |
| WO | WO 02/017880 | 5/2002 |

OTHER PUBLICATIONS

Bohl et al., "Nitric Oxide-Releasing Materials for the Prevention of Thrombosis and Restenosis", Proceed. Int'l. Sym. Control. Rel. Bioact. Mater., 2000, 143-144, vol. 27.

Bohl et al., "Nitric Oxide Producing Materials: A Potential Therapy for Thrombosis and Restenosis", Proceed. Int'l. Sym. Control. Rel. Bioact. Mater., 1999, 56-57, vol. 26.

Bohl et al., "Nitric Oxide-Releasing Hydrogels for the Prevention of Thrombosis and Restenosis", Circulation, Oct. 31, 2000; II.734, vol. 102, No. 18 (Abstract Only).

Cohn et al, "Biodegradable PEO/PLA block polymers", J. Biomed. Mater. Res., 1988, 993-1009, vol. 22.

Cooke et al., "Antiatherogenic Effects of L-Arginine in the Hypercholesterolemic Rabbit", J. Clin. Invest., 1992, 1168-1172, vol. 90.

De Graaf et al., "Nitric Oxide Functions as an Inhibitor of Platelet Adhesion Under Flow Conditions", Circulation, 1992, 2284-2290, vol. 85.

De Meyer et al., "Effect of Nitric Oxide Donors on Neointima Formation and Vascular Reactivity in the Collared Carotid Artery of Rabbits", J. Cardiovasc. Res., 1995, 272-279, vol. 26.

Diodati et al., "Complexes of Nitric Oxide with Nucleophiles as Agents for the Controlled Biological Release of Nitric Oxide: Hemodynamic Effect in the Rabbit", J. Cardiovasc. Pharm., 1993, 287-292, vol. 22.

Diodati et al., "Complexes of Nitric Oxide with Nucleophiles as Agents for the Controlled Biological Release of Nitric Oxide: Antiplatelet Effect", Throm. Haem., 1993, 654-658, 1993.

Garg et al., "Nitric Oxide-Generating Vasodilators and 8-Bromo Cyclic Guanosine Monophosphate Inhibit Mitogenesis and Proliferation of Cultured Rat Vascular Smooth Muscle Cells", J. Clin. Invest., 1989, 1774-1777, vol. 83.

Greenhalgh, "The Role of Growth Factors in Wound Healing", J. Trauma, 1996, 159-167, vol. 41.

Heller et al., "Nitric Oxide Inhibits Proliferation of Human Endothelial Cells via a Mechanism Independent of cGMP", Atherosclerosis, 1999, 49-57, vol. 144.

Hern et al., "Incorporation of Adhesion Peptides into Nonadhesive Hydrogels Useful for Tissue Resurfacing", J. Biomed. Mater. Res., 1998, 266-276, vol. 39.

Holland et al., Polymers for Biodegradable Medical Devices. 1. The Potential of Polyesters as Controlled Macromolecular Release Systems, 1986, 155-180, vol. 4.

Ignarro et al., "Mechanism of Vascular Smooth Muscle Relaxation by Organic Nitrates, Nitrites, Nitroprusside and Nitric Oxide: Evidence for the Involvement of S-Nitrosothiols as Active Intermediates", J. Pharmacol. Exp. Ther., 1981, 739-749, vol. 218.

Kwon et al., "Inhibition of Tumor Cell Ribonucleotide Reductase by Macrophage-derived Nitric Oxide", J. Exp. Med., 1991, 761-767, vol. 174.

Lefer et al., "Antineutrophil and Myocardial Protecting Actions of a Novel Nitric Oxide Donor After Acute Myocardial Ischemia and Reperfusion in Dogs", Circulation, 1993, 2337-2350, vol. 88.

Legrand et al., "Preclinical Promise of Becaplermin (rhPDGF-BB) in Wound Healing", Am. J. Surg., 1998, 48S-54S, vol. 176.

Lepoivre et al., "Inactivation of Ribonucleotide Reductase by Nitric Oxide", Biochem. Biophys. Res. Comm., 1991, 442-448, vol. 179.

Lin et al., "Nitric Oxide-Based Molecular Strategies for Restenosis Therapy" in Expert Opinion on Therapeutic Patients, 15: 483-495 (2005).

Mann et al., "Tethered-TGF-βIncreases Extracellular Matrix Production of Vascular Smooth Muscle Cells", Biomaterials, 2001, 439-444, vol. 22.

Maragos et al., "Nitric Oxide/Nucleophile Complexes Inhibit the in Vitro Proliferation of A375 Melanoma Cells via Nitric Oxide Release", Cancer Res., 1993, 564-568, vol. 53.

Martinez-De Jesus et al., "Randomized Single-Blind Trial of Topical Ketanserin for Healing Acceleration of Diabetic Foot Ulcers", Arch. Med. Res., 1997, 95-99, vol. Spring 28 (1) (Abstract only).

Mathews et al., "Biological Activity of S-Nitrosothiols: The Role of Nitric Oxide", J. Pharmacol. Exp. Therap., 1993, 1529-1537, vol. 267.

Moro et al., "cGMP Mediates the Vascular and Platelet Actions of Nitric Oxide: Confirmation Using an Inhibitor of the Soluble Guanylyl Cyclase", Proc. Natl. Acad. Sci. USA, 1996, 1480-1485, vol. 93.

Rodomski et al., "Comparative Pharmacology of Endothelium-Derived Relaxing Factor, Nitric Oxide and Prostacyclin in Platelets", Br. J. Pharmacol., 1987, 181-187, vol. 92.

Sarkar et al., "Nitric Oxide Inhibition of Endothelial Cell Mitogenesis and Proliferation", Surgery, 1995, 274-279, vol. 118.

Sawhney et al., "Rapidly Degraded Terpolymers of dl-Lactide, Glycolide, and ε-Caprolactone with Increased Hydrophilicity by Copolymerization with Polyethers", J. Biomed. Res., 1990, 1397-1411, vol. 24.

Scott-Burden et al., "Extracellular Matrix: Differential Influence on Growth and Biosynthesis Patterns of Vascular Smooth Muscle Cells from SHR and WKY Rats", J. Cell Physiol., 1989, 267-274, vol. 141.

Scott-Burden et al., "Genetically Engineered Smooth Muscle Cells as Linings to Improve the Biocompatibility of Cardiovascular Prostheses", Circulation, 1996,II235-238, vol. 94 (9 Suppl.).

Smith et al., "Nitric Oxide-Releasing Polymers Containing the [N(O)NO] Group", J. Med. Chem., 1996, 1148-1156, vol. 39.

Spilizewski et al., "The Effect of Hydrocortisone Acetate Loaded Poly (DL-Lactide) Films on the Inflammatory Response", J. Control. Rel., 1985, 197-203, vol. 2.

Stuehr et al., "Nitric Oxide—A Macrophage Product Responsible for Cytostasis and Respiratory Inhibition in Tumor Target Cells", J. Exp. Med., 1989, 1543-1555, vol. 169.

West et al., "Bioactive Polymers", Synthetic Biodegradable Polymer Scaffolds, 1997, 83-95.

Williams et al., "Safety and Tolerability of Intravenous-to-Oral Treatment and Single-Dose Intravenous or Oral Prophylaxis with Trovafloxacin", Am. J. Surg., 1998, 74S-79S, vol. 176.

Wieman et al., "Efficacy and Safety of a Topical Gel Formulation of Recombinant Human Platelet-Derived Growth Factor-BB (Becaplermin) in Patients with Chronic Neuropathic Diabetic Ulcers", Diabetes Care, 1998, 822-827, vol. 21.

Ziche et al., "Nitric Oxide Promotes DNA Synthesis and Cyclic GMP Formation in Endothelial Cells from Postcapillary Venules", Biochem. Biophys. Res. Comm., 1993, 1198-1203, vol. 192.

Abstract, Derwent WPI, HU 9801673 A1 (Aug. 28, 2000), (Cycl-N) Cyclolab Ciklodextrin Kutato Fejleszto.

Database WPI, *Derwent Publications, Ltd.*, London, GB, Section Ch, Week 200061, AN 2000-630208.

* cited by examiner

* INDICATES DIFFERENT CYSNO CONCENTRATION THAN USED FOR HYDROGEL

NITRIC OXIDE-PRODUCING HYDROGEL MATERIALS

CROSS-REFERENCE TO RELATED APPLICATIONS

This application is a divisional application of U.S. application Ser. No. 10/129,418, filed May 17, 2002 now U.S. Pat. No. 7,052,711, which is a National Stage of International PCT Application No. PCT/US01/27414, filed Sep. 4, 2001, which is a continuation-in-part of U.S. application Ser. No. 09/653,406, filed Sep. 1, 2000 now U.S. Pat. No. 7,279,176, which claims the benefit of U.S. Provisional Application No. 60/152,054, filed Sep. 2, 1999.

FIELD OF THE INVENTION

The present invention relates to polymerizable hydrogel materials that produce physiologically relevant amounts of nitric oxide (NO).

BACKGROUND OF THE INVENTION

Endothelial cells, normally present as a monolayer in the intimal layer of the arterial wall, are believed to play an important role in the regulation of smooth muscle cell (SMC) proliferation in vivo. Endothelial cells are seriously disrupted by most forms of vascular injury, including that caused by percutaneous transluminal coronary angioplasty and similar procedures. Approximately 35-50% of patients treated by percutaneous transluminal coronary angioplasty experience clinically significant renarrowing of the artery, or restenosis, within six months of the initial treatment. Restenosis is due, at least in part, to migration and proliferation of smooth muscle cells in the arterial wall along with increases in secretion of matrix proteins to form an obstructive neointimal layer within the arterial wall. Similar issues limit the performance of vascular grafts. The processes that regulate arterial wound healing following vascular injury, such as that caused by angioplasty, are as yet poorly understood, but are believed to involve a complex cascade of blood and vessel wall-derived factors.

Numerous factors that stimulate intimal thickening and restenosis have been identified through administration of exogenous proteins, genetic alteration of cells, or through the blockade of certain signals using antibodies or other specific growth factor inhibitors. These smooth muscle cell mitogens and chemoattractants derive from both the blood or thrombus formation and from the vessel wall itself. Endothelial cells produce a number of substances known to down-regulate smooth muscle cell proliferation, including heparin sulfate, prostacyclin (PG12), and NO.

NO is an endothelium-derived target molecule useful for the prevention of restenosis because, in addition to limiting the proliferation of smooth muscle cells (Garg et al., (1989) *J. Clin. Invest.*, 83:1774-7), NO reduces platelet aggregation (de Graaf et al., (1992) *Circulation*, 85:2284-90; Radomski et al., (1987) *Br. J Pharmacol.*, 92:181-7), increases endothelial cell proliferation (Ziche et al., (1993) *Biochem. Biophys. Res. Comm.*, 192:1198-1203), and attenuates leukocyte adhesion (Lefer et al., (1993) *Circulation*, 88:2337-50), all of which are highly desirable for the reduction of intimal thickening and restenosis (Loscalzo, (1996) *Clin. Appl. Thromb. Hemostas.*, 2:7-10). Because of the complexity of the restenotic process, approaches that act upon multiple targets are the most likely to be successful.

The mechanisms whereby NO affects these multiple responses are not fully understood as yet, but it is known that NO activates soluble guanylate cyclase by binding to its heme moiety, thereby elevating the levels of cyclic guanosine monophosphate (cGMP), an intracellular second messenger with multiple cellular effects (Moro et al., (1996) *Proc. Natl. Acad. Sci. USA*, 93:1480-5). The effects of NO can often be mimicked by the administration of cGMP or more stable derivatives of cGMP (Garg et al., (1989) *J. Clin. Invest.*, 83:1774-7). In addition, NO has been found to inhibit ribonucleotide reductase, an enzyme that converts ribonucleotides into deoxy ribonucleotides, thus significantly impacting DNA synthesis (Lepoivre et al., (1991) *Biochem. Biophys. Res. Comm.*, 179:442-8; Kwon et al., (1991) *J. Exp. Med.*, 174:761-7), as well as several enzymes involved in cellular respiration (Stuehr et al., (1989) *J. Exp. Med.*, 169:1543-55).

A number of molecules that produce NO under physiological conditions (NO donors) have been identified and evaluated both in vitro and in vivo. NO donor molecules exert biological effects mimicking those of NO and include S-nitrosothiols (Diodati et al, (1993) *Thromb. Haem.*, 70:654-8; Lefer et al., (1993) *Circulation*, 88:2337-50; DeMeyer et al., (1995) *J. Cardiovasc. Pharmacol.*, 26:272-9), organic nitrates (Ignarro et al., (1981) *J. Pharmacol. Exp. Ther.*, 218: 739-49), and complexes of NO with nucleophiles (Diodati et al., (1993) *Thromb. Haem.*, 70:654-8; Diodati et al., (1993) *J. Cardiovasc. Pharmacol.*, 22:287-92; Maragos et al., (1993) *Cancer Res.*, 53:564-8). Most of these have been low molecular weight molecules that are administered systemically and have short half-lives under physiologic conditions, thus exerting effects upon numerous tissue types with a brief period of activity. In addition, L-arginine is often thought of as a NO donor, as L-arginine is a substrate for NO synthase, and thus adnlinistration of L-arginine increases endogenous NO production and elicits responses similar to those caused by NO donors in most cases (Cooke et al., (1992) *J. Clin. Invest.*, 90:1168-72).

The development of NO-releasing polymers containing NO/nucleophile complexes has been reported by Smith et al., (1996) *J. Med. Chem.*, 39:1148-56. These materials were capable of releasing NO for as long as five weeks in vitro and were able to limit smooth muscle cell proliferation in culture and to reduce platelet adherence to vascular graft materials in an arterio-venous shunt model. These materials show promise for numerous clinical applications where localized NO production would be desired, such as anti-thrombotic coating materials for catheters, but probably will not be useful for the direct treatment of tissues in vivo as these materials suffer from a number of disadvantages. These polymers may be produced as films, powders, or microspheres, but they cannot be formed in situ in direct contact with cells and tissues, thus making it difficult to strictly localize NO treatment to a tissue and potentially causing issues with the retention of the polymer at the site of application. The formulation issues will also make local administration during laparoscopic or catheter-based procedures difficult or impossible. Additionally, biocompatibility of the base polymer is a serious issue for implantable, NO-releasing polymers, especially those intended for long-term use, as inflammatory and thrombotic responses may develop after the cessation of NO release.

With respect to chronic wound healing, approaches that are common today are typically based on simple wound care regimens involving debridement, cleaning, and application of moist dressings (Thomas S, Leigh (1998). WOUND DRESSINGS. WOUNDS: BIOLOGY AND MANAGEMENT, D. Leaper and K. Harding. New York, N.Y., Oxford University Press). More advanced dressings such as topical gels containing growth factors have resulted in enhanced healing rates in some clinical studies (Wieman T, Smiell J, Su Y. Efficacy and safety of a topical gel formulation of recombinant human platelet-derived growth factor-BB (beclapermin) in patients with non-healing diabetic ulcers: a phase III randomized, placebo-controlled, double-blind study. *Diabetes Care* 1998; 21: 822-827; Wieman T J and the Beclapermin Gel Studies Group. Clinical efficacy of Beclapermin (rhPDGF-BB) Gel. *Am J Surg* 1998; 176: 74S-79S; Martinez-de Jesus F R, Morales-Guzman M, Gastaneda M, Perez-Morales A, Garcia-Alsono J, Mendiola-Segura L. Randomized single-blind trial of topical ketanserin for healing acceleration of diabetic foot ulcers. *Arch Med Res* 1997; 28: 95-99), however on the whole these treatments are difficult to apply and are often too expensive for application to large, chronic wounds. Additionally, not all chronic wounds display growth factor deficiencies, and other mechanisms such as rapid degradation by wound proteinases may be involved in the reduction of growth factor levels observed in many chronic wounds. Many chronic wounds are unresponsive to growth factor therapy (Greenhalgh D. The role of growth factors, in wound healing. *J Trauma* 1996; 41: 159-167).

With respect to proliferation of endothelial cells, it has been shown that the presence of NO decreases endothelial cell proliferation. See, for example, Heller, R., Polack, T., Grabner, R., Till, U. (1999) "Nitric oxide inhibits proliferation of human endothelial cells via a mechanism independent of cGMP", *Atherosclerosis*, 144:49-57; and Sarkar, R., Webb, R. C., Stanley, J. C. (1995) "Nitric oxide inhibition of endothelial cell mitogenesis and proliferation", *Surgery*, 118:274-9. However, these studies utilized very high doses of NO-releasing drugs, which may account for the decreased endothelial cell proliferation. Additionally, previous researchers have found it difficult to seed endothelial cells onto devices: Scott-Burden, T., Tock, C.L., Schwarz, J. J., Casscells, S. W., Engler, D. A. (1996) "Genetically engineered smooth muscle cells as linings to improve the biocompatibility of cardiovascular prostheses", *Circulation*, 94:235-8.

It is believed by the inventors that the development of materials that encourage the proliferation and/or migration of endothelial cells should enhance the growth of endogenous endothelial cells from tissue surrounding an implant onto the implant surface. Therefore, applicants propose that endothelialization of blood-contacting implants, such as stents, grafts, and ventricular assist devices, may significantly improve device performance by decreasing thrombogenicity and smooth muscle cell proliferation.

It would be more efficient if NO releasing compounds or compounds modulating NO levels could be administered solely to the site in need of treatment, and in some cases, reduce or eliminate side effects due to systemic administration of the agents, particularly over prolonged time periods.

SUMMARY OF THE INVENTION

Biocompatible polymeric materials releasing or producing physiological amounts of nitric oxide (NO) for prolonged periods of time are described herein. The biocompatible polymeric materials are applied to sites on or in a patient in need of treatment thereof for disorders such as restenosis, thrombosis, asthma, wound healing, arthritis, penile erectile dysfunction or other conditions where NO plays a significant role. The polymeric materials can be formed into films, coatings, or microparticles for application to medical devices, such as stents, vascular grafts and catheters. The polymeric materials can also be applied directly to biological tissues and can be polymerized in situ.

The polymers are formed of macromers, which may include biodegradable regions, and have bound thereto groups that are released in situ to elevate or otherwise modulate NO levels at the site where treatment is needed. The macromers can form a homo or hetero-dispersion or solution, which is polymerized to form a polymeric material, that in the latter case can be a semi-interpenetrating network or interpenetrating network. Compounds to be released can be physically entrapped, covalently or ionically bound to macromer, or actually form a part of the polymeric material. Hydrogels can be formed by ionic and/or covalent crosslinking. Other active agents, including therapeutic, prophylactic, or diagnostic agents, can also be included within the polymeric material.

BRIEF DESCRIPTION OF DRAWINGS

FIG. 8A, % of control cell number, hydrogel formulation. FIG. 8B, % of control cell number, soluble polymer.

DETAILED DESCRIPTION OF THE INVENTION

Figure 1:
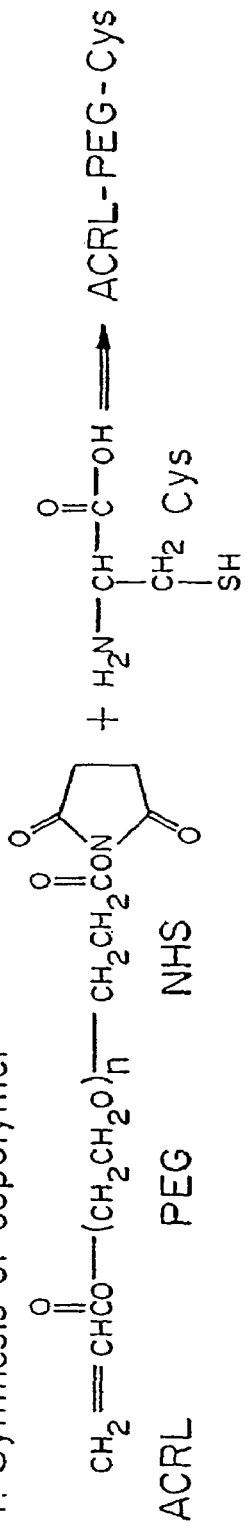
FIG. 1 is a schematic of the synthesis of S-nitrosocysteine hydrogels (Acryloyl-PEG-Cys-NO).
Figure 1:
Figure 1:
Figure 1:
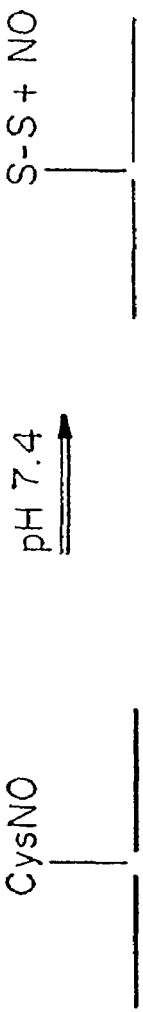

Biocompatible polymeric materials releasing or producing physiological amounts of nitric oxide (NO) and methods of use for the treatment of disorders such as restenosis, thrombosis, asthma, wound healing, arthritis, penile erectile dysfunction, or other conditions where NO plays a significant role, are provided herein.

I. Polymeric Materials for Release of NO

The polymeric materials are biocompatible and release or produce NO. In various preferred embodiments, the polymers are also biodegradable, form hydrogels, polymerize in situ and are tissue adherent. The polymeric materials can also be formed into films, coatings, or microparticles for application to medical devices, such as stents, vascular grafts and catheters. These properties are conferred by the selection of the macromer components as well as addition of various groups to the components.

The term "polymerizable" means that the regions have the capacity to form additional covalent bonds resulting in macromer interlinking, for example, carbon-carbon double bonds of acrylate-type molecules. Such polymerization is characteristically initiated by free-radical formation resulting from photon absorption of certain dyes and chemical compounds to ultimately produce free-radicals, although polymerization can be obtained using other methods and reagents known to those skilled in the art.

All chemicals mentioned herein are obtainable from commercial chemical companies such as Sigma-Aldrich Chemical Corp. (St. Louis, Mo.), unless otherwise specified.

A. Polymeric Materials

The polymeric materials described herein must be biocompatible, i.e., not eliciting a significant or unacceptable toxic or immunogenic response following administration to or implantation into an individual.

A number of polymeric materials are known which are biocompatible, including both natural and synthetic polymers. Examples include proteins (of the same origin as the recipient), polysaccharides such as chondroitin sulfate and hyaluronic acid, polyurethanes, polyesters, polyamides, and acrylates. Polymers can be degradable or non-degradable.

The preferred polymeric materials will be selected based on a combination of properties conferred by the various components, which may include at least one water soluble region, such as polyethylene glycol (PEG) or polyvinyl alcohol (PVA), at least one biodegradable region such as regions that degrade hydrolytically, and at least one group that can be used to polymerize the macromers in situ.

One advantage to using the hydrogels described herein is the ability to covalently attach a variety of bioactive molecules. As demonstrated by the stimulation of proliferation of endothelial cells cultured on hydrogels containing both a cell adhesion peptide sequence and an NO donor (FIG. 13), many factors can be combined within the same hydrogel in order to design a material that will perform optimally for the desired application. Examples of cell adhesion peptide sequences (also referred to herein as cell adhesion ligands) include RGD, RGDS, REDV (the letters indicate the single letter amino acid nomenclature known to those skilled in the art), and other sequences that are endothelial cell-specific. The cell adhesion ligands are used to specifically target the adhesion, proliferation, and migration of certain cells. The cell adhesion ligand may be a peptide, protein, carbohydrate, or other type of moiety that will assist in seeding cells onto devices. For example, other bioactive molecules such as growth factors have also been shown to retain their efficacy when covalently attached to PEG (Mann B, Schmedlen R, West J. Tethered-TGF-beta increases extracellular matrix production of vascular smooth muscle cells. *Biomaterials* 2001; 22: 439-444). Thus, there exists the possibility of creating a multifunctional material that combines NO therapy with at least one cell-specific adhesion ligand or growth factor in order to achieve specific results.

Water-Soluble and/or Tissue Adhesive Regions

A variety of water soluble materials can be incorporated into the polymers. The term "at least substantially water soluble" is indicative that the solubility should be at least about 5 g/100 ml of aqueous solution. In preferred embodiments, the core water soluble region can consist of poly (ethylene glycol), referred to herein as "PEG", poly(ethylene oxide), poly(vinyl acetate), poly(vinyl alcohol), referred to herein as "PVA", poly(vinylpyrrolidone), poly(ethyloxazoline), poly(ethylene oxide)-co-poly(propyleneoxide) block copolymers, polysaccharides or carbohydrates such as hyaluronic acid, dextran, heparin sulfate, chondroitin sulfate, heparin, or alginate, or proteins such as gelatin, collagen, albumin, or ovalbumin.

Hydrophilic (i.e., water soluble) regions will generally be tissue adhesive. Both hydrophobic and hydrophilic polymers which include a large number of exposed carboxylic groups are tissue adhesive or bioadhesive. Ligands such as RGD peptides and lectins which bind to carbohydrate molecules on cells can also be bound to the polymer to increase tissue adhesiveness.

Degradable Regions

Polyesters (Holland et al., 1986 *Controlled Release*, 4:155-180) of α-hydroxy acids (viz., lactic acid, glycolic acid), are the most widely used biodegradable materials for applications ranging from closure devices (sutures and staples) to drug delivery systems (U.S. Pat. No. 4,741,337 to Smith et al.; Spilizewski et al., 1985 *J. Control. Rel.* 2:197-203). In addition to the poly(hydroxy acids), several other polymers are known to biodegrade, including polyanhydrides and polyorthoesters, which take advantage of labile backbone linkages, as reported by Domb et al., 1989 *Macromolecules*, 22:3200; Heller et al., 1990 *Biodegradable Polymners as Drug Delivery Systems*, Chasin, M. and Langer, R., Eds., Dekker, New York, 121-161. Polyaminoacids have also been synthesized since it is desirable to have polymers that degrade into naturally occurring materials for in vivo use.

The time required for a polymer to degrade can be tailored by selecting appropriate monomers. Differences in crystallinity also alter degradation rates. Due to the relatively hydrophobic nature of these polymers, actual mass loss only begins when the oligomeric fragments are small enough to be water soluble. Hence, initial polymer molecular weight influences the degradation rate.

The biodegradable region is preferably hydrolyzable under in vivo conditions. Hydrolyzable groups may be polymers and oligomers of glycolide, lactide, $\epsilon$-caprolactone, other $\alpha$-hydroxy acids, and other biologically degradable polymers that yield materials that are non-toxic or present as normal metabolites in the body. Preferred poly($\alpha$-hydroxy acid)s are poly(glycolic acid), poly(DL-lactic acid) and poly(L-lactic acid). Other useful materials include poly(amino acids), poly (anhydrides), poly(orthoesters), and poly(phosphoesters). Polylactones such as poly($\epsilon$-caprolactone), poly($\epsilon$-caprolactone), poly($\delta$-valerolactone) and poly(gamma-butyrolactone), for example, are also useful.

Biodegradable regions can also be constructed from polymers or monomers using linkages susceptible to biodegradation by enzymes, such as ester, peptide, anhydride, orthoester, and phosphoester bonds. Degradable materials of biological origin are well known, for example, crosslinked gelatin. Hyaluronic acid has been crosslinked and used as a degradable swelling polymer for biomedical applications (U.S. Pat. No. 4,987,744 to della Valle et al., U.S. Pat. No. 4,957,744 to Della Valle et al. (1991) *Polym. Mater. Sci. Eng.*, 62:731-735).

Biodegradable Hydrogels

A number of polymers have been described which include both water soluble regions and biodegradable regions. Sawhney et al., (1990) *J. Biomed. Mater. Res.* 24:1397-1411, copolymerized lactide, glycolide and $\epsilon$-caprolactone with PEG to increase its hydrophilicity and degradation rate. U.S. Pat. No. 4,716,203 to Casey et al. (1987) synthesized a PGA-PEG-PGA block copolymer, with PEG content ranging from 5-25% by mass. U.S. Pat. No. 4,716,203 to Casey et al. (1987) also reports synthesis of PGA-PEG diblock copolymers, again with PEG ranging from 5-25%. U.S. Pat. No. 4,526,938 to Churchill et al. (1985) described noncrosslinked materials with MW in excess of 5,000, based on similar compositions with PEG; although these materials are not water soluble. Cohn et al. (1988) *J. Biomed. Mater. Res.* 22:993-1009 described PLA-PEG copolymers that swell in water up to 60%; these polymers also are not soluble in water, and are not crosslinked. The features that are common to these materials are that they use both water-soluble polymers and degradable polymers, and that they are insoluble in water, collectively swelling up to about 60%.

U.S. Pat. No. 5,410,016 issued on Apr. 25, 1995 to Hubbell, et al., describes materials which are based on polyethylene glycol (PEG), because of its high biocompatible and thromboresistant nature, with short polylactide extensions to impart biodegradation and acrylate termini to allow rapid photopolymerization without observable heat production. These materials are readily modified to produce hydrogels which release or produce NO.

The polymerizable regions are separated by at least one degradable region to facilitate uniform degradation in vivo. There are several variations of these polymers. For example, the polymerizable regions can be attached directly to degradable extensions or indirectly via water soluble nondegradable sections so long as the polymerizable regions are separated by a degradable section. For example, if the macromer composition contains a simple water soluble region coupled to a degradable region, one polymerizable region may be attached to the water soluble region and the other attached to the degradable extension or region. In another embodiment, the water soluble region forms the central core of the macromer composition and has at least two degradable regions attached to the core. At least two polymerizable regions are attached to the degradable regions so that, upon degradation, the polyrnerizable regions, particularly in the polymerized gel form, are separated. Conversely, if the central core of the macromer composition is formed by a degradable region, at least two water soluble regions can be attached to the core and polymerizable regions can be attached to each water soluble region. The net result will be the same after gel formation and exposure to in vivo degradation conditions.

In another embodiment, the macromer composition has a water soluble backbone region and a degradable region affixed to the macromer backbone. At least two polymerizable regions are attached to the degradable regions, so that they are separated upon degradation, resulting in gel product dissolution. In a further embodiment, the macromer backbone is formed of a nondegradable backbone having water soluble regions as branches or grafts attached to the degradable backbone. Two or more polymerizable regions are attached to the water soluble branches or grafts. In another variation, the backbone may be star shaped, which may include a water soluble region, a biodegradable region or a water soluble region which is also biodegradable. In this general embodiment, the star region contains either water soluble or biodegradable branches or grafts with polymerizable regions attached thereto. Again, the polymerizable regions must be separated at some point by a degradable region.

Polymerizable Groups.

The polymerizable regions may be polymerizable by photoinitiation by free radical generation, most preferably in the visible or long wavelength ultraviolet radiation. The preferred polymerizable regions are acrylates, diacrylates, oligoacrylates, dimethacrylates, oligomethoacrylates, or other biologically acceptable photopolymerizable groups. A preferred tertiary amine is triethanol amine.

Useful photoinitiators are those which can be used to initiate by free radical generation polymerization of the macromers without cytotoxicity and within a short time frame, minutes at most and most preferably seconds. Preferred dyes as initiators of choice for long wavelength ultraviolet (LWUV) light initiation are ethyl eosin, 2,2-dimethoxy-2-phenyl acetophenone, other acetophenone derivatives, other eosin derivatives, such as eosin Y, and camphorquinone. In all cases, crosslinking and polymerization are initiated among copolymers by a light-activated free-radical polymerization initiator such as 2,2-dimethoxy-2-phenylacetophenone or a combination of ethyl eosin ($10^{-4}$-$10^{-2}$ mM) and triethanolamine (0.001 to 0.1 M), for example.

The choice of the photoinitiator is largely dependent on the photopolymerizable regions. For example, when the macromer includes at least one carbon-carbon double bond, light absorption by the dye causes the dye to assume a triplet state, the triplet state subsequently reacting with the amine to form a free radical which initiates polymerization. Preferred dyes for use with these materials include eosin dye and initiators such as 2,2-dimethyl-2-phenylacetophenone, 2-methoxy-2-phenylacetophenone, and camphorquinone. Using such initiators, coplymers may be polymerized in situ by long wavelength ultraviolet light or by laser light of about 514 nm, for example.

Initiation of polymerization is accomplished by irradiation with light at a wavelength of between about 200-700 nm, most preferably in the long wavelength ultraviolet range or visible range, 320 nm or higher, most preferably about 514 nm or 365 nm.

There are several photooxidizable and photoreducible dyes that may be used to initiate polymerization. These include acridine dyes, for example, acriblarine; thiazine dyes, for example, thionine; xanthine dyes, for example, rose bengal; and phenazine dyes, for example, methylene blue. These are used with cocatalysts such as amines, for example, triethanolamine; sulphur compounds, for example, $RSO_2R_1$; heterocycles, for example, imidazole; enolates; organometallics; and other compounds, such as N-phenyl glycine. Other initiators include camphorquinones and acetophenone derivatives.

Thermal polymerization initiator systems may also be used. Such systems that are unstable at 37° C. and would initiate free radical polymerization at physiological temperatures include, for example, potassium persulfate, with or without tetramethyl ethylenediamine; benzoylperoxide, with or without triethanolamine; and ammonium persulfate with sodium bisulfite.

Other initiation chemistries may be used besides photoinitiation. These include, for example, water and amine initiation schemes with isocyanate or isothiocyanate containing macromers used as the polymerizable regions.

Preferred Embodiments

In a preferred embodiment, the polymeric materials in the macromer composition are polymerizable and at least substantially water soluble. A first macromer includes at least one water soluble region, at least one NO carrying region, and at least one free radical-polymerizable region. A second macromer includes at least one water soluble region and at least two free radical polymerizable regions. The regions can, in some embodiments, be both water soluble and biodegradable. The macromer composition is polymerized by exposure of the polymerizable regions to free radicals generated, for example, by photosensitive chemicals and dyes.

Examples of these macromers are PVA or PEG. The choice of appropriate end caps permits rapid polymerization and gelation. Acrylates are preferred because they can be polymerized using several initiating systems, e.g., an eosin dye, by brief exposure to ultraviolet or visible light. A PEG central structural unit (core) is preferred on the basis of its high hydrophilicity and water solubility, accompanied by excellent biocompatibility. A short oligo or poly($\alpha$-hydroxy acid), such as polyglycolic acid, can be used as a biodegradable chain extension because it rapidly degrades by hydrolysis of the ester linkage into glycolic acid, a harmless metabolite. Although highly crystalline polyglycolic acid is insoluble in water and most common organic solvents, the entire macromer composition is water-soluble and can be rapidly gelled into a biodegradable network while in contact with aqueous tissue fluids. Such networks can be used to entrap and homogeneously disperse water-soluble drugs and enzymes and to deliver them at a controlled rate. Further, they may be used to entrap particulate suspensions of water-insoluble drugs. Other preferred chain extensions are polylactic acid, polycaprolactone, polyorthoesters, and polyanhydrides. Polypeptides may also be used. Such "polymeric" blocks should be understood to included dimeric, trimeric, and oligomeric blocks.

PVA contains many pendant hydroxyl groups. These hydroxyl groups are easily reacted to form side chains such as various crosslinking agents and nitric oxide donors. PVA is water soluble and has excellent biocompatiblity. Modification of PVA to attach methacrylate groups via a diacetal bond with the pendant hydroxyl groups and addition of an appropriate photoinitiator enables the PVA to be photopolymerized to form hydrogels under long wavelength UV light. In another preferred embodiment, the hydrogel is formed from modified polyvinyl alcohol (PVA) macromers, such as those described in U.S. Pat. Nos. 5,508,317, 5,665,840, 5,849,841, 5,932,674, 6,011,077, 5,939,489, and 5,807,927. The macromers disclosed in U.S. Pat. No. 5,508,317, for example, are PVA prepolymers modified with pendant crosslinkable groups, such as acrylamide groups containing crosslinkable olefinically unsaturated groups. These macromers can be polymerized by photopolymerization or redox free radical polymerization, for example. Several embodiments of the macromers of the invention are disclosed herein describing formulations for photopolymerizable macromers. However, one of skill in the art, after studying this disclosure, would know how to make and use macromers formulated for other methods of polymerization. The starting polymers are, in particular, derivatives of polyvinyl alcohol or copolymers of vinyl alcohol that contain, for example, a 1,3-diol skeleton. The crosslinkable group or the further modifier can be bonded to the starting polymer skeleton in various ways, for example through a certain percentage of the 1,3-diol units being modified to give a 1,3-dioxane, which contains a crosslinkable radical, or a further modifier in the 2-position. Another possibility is for a certain percentage of hydroxyl groups in the starting polymer to be esterified by means of an unsaturated organic acid, these ester-bonded radicals containing a crosslinkable group. The hydrophobicity of these macromers can be increased by substituting some of the pendant hydroxyl groups with more hydrophobic substituents. The properties of the macromers, such as hydrophobicity, can also be modified by incorporating a co-monomer in the macromer backbone. The macromers can also be formed having pendant groups crosslinkable by other means.

B. NO groups or Modulating Compounds

A number of molecules that produce NO under physiological conditions (NO donors) have been identified and evaluated both in vitro and in vivo, including S-nitrosothiols, organic nitrates, and complexes of NO with nucleophiles. L-arginine is a NO donor, since L-arginine is a substrate for NO synthase, and thus administration of L-arginine increases endogenous NO production and elicits responses similar to those caused by NO donors in most cases. Other NO donors include molsidomine, CAS754, SPM-5185, and SIN-1. Other compounds capable of producing and/or donating NO may also be used. These include organic nitrates, nitrosylating compounds, nitrosoesters, and L-arginine.

The molecules which produce NO, or release or generate NO, are preferably attached to regions containing nucleophiles and/or thiols such as S-nitrosothiols capable of forming a complex with NO.

C. Prophylactic, Therapeutic and Diagnostic Agents

The polymeric materials can also be used for drug delivery, preferably localized release of prophylactic, therapeutic or diagnostic agents at the site where the materials are needed, although the polymeric materials can be loaded with agent to be released systemically. These agents include proteins or peptides, polysaccharides, nucleic acid molecules, and simple organic molecules, both natural and synthetic. Representative materials include antibiotics, antivirals, and antifungal drugs, anti-inflammatories (steroidal or non-steroidal), hormones, growth factors, cytokines, neuroactive agents, vasoconstrictors and other molecules involved in the cardiovascular responses, enzymes, antineoplastic agents, local anesthetics, antiangiogenic agents, antibodies, drugs affecting reproductive organs, and oligonucleotides such as antisense oligonucleotides. Diagnostic materials may be radioactive, bound to or cleave a chromogenic substrate, or detectable by ultrasound, x-ray, MRI, or other standard imaging means.

These agents can be mixed with macromer prior to polymerization, applied into or onto the polymer, or bound to the macromer prior to or at the time of polymerization, either covalently or ionically, so that the agent is released by degradation (enzymatic or hydrolytic) or diffusion at the site where the polymer is applied.

II. Methods of Use

A. Coatings; Films; Microparticles

Although described primarily with respect to ill vivo treatment, it is apparent that the polymeric materials described herein can be used in cell culture, on cell culture substrates, or as coatings on medical implants or devices such as stents, vascular grafts, or catheters, or formed using standard techniques into microparticles or other types of formulations which may be used in or administered to a patient.

For example, coatings on medical devices or implants may be used when the proliferation of endothelial cells over the medical device would prolong the use and safety of the device. One of skill in the art may envision many such uses. An example is found in dialysis. The coating would allow endothelial proliferation over the graft used during a dialysis session, thereby prolonging the usable time for each graft, thus delaying the need for a kidney transplant. Coatings may provide other advantages seen upon local delivery of NO such as decreased proliferation of smooth muscle cells and decreased platelet aggregation.

B. Therapeutic Applications

Polymeric materials capable of releasing physiological amounts of NO for prolonged periods of time can be applied to sites on or in a patient in need of treatment thereof. Representative disorders or conditions that can be treated with NO include restenosis, thrombosis, asthma, wound healing, arthritis, and penile or female erectile dysfunction. The material can be applied as a macromer solution and polymerized in situ or polymerization can be initiated prior to application. The polymeric materials can also be coated onto medical devices.

Wound Healing

The formulations are particularly useful for treatment of all types of wounds, including burns, surgical wounds, and open leg and foot wounds. There are generally three types of open leg wounds, termed ulcers: venous stasis ulcers, generally seen in sedentary elderly people when blood flow to the leg becomes sluggish; decubitus ulcers, also termed pressure sores or bed sores, which occurs most often in people who are bedridden and are unable to frequently change position; and diabetic foot ulcers, caused by poor blood circulation to the feet. Due to the aging of the population, there will likely be a greater demand for effective and user friendly wound treatments in the near future The term "wound" as used herein refers to all types of tissue injuries, including those inflicted by surgery and trauma, including burns, as well as injuries from chronic or acute medical conditions, such as atherosclerosis or diabetes.

Example 13 shows that exogenous NO released from hydrogel wound dressings may enhance wound healing of chronic wounds. In vivo results examining effects of NO in the diabetic wound model suggest that the most useful parameters for assessing efficacy of wound healing are granulation tissue thickness and matrix production. Similar findings have been reported in studies examining the effect of growth factors on wound healing in animals (Greenhalgh D. The role of growth factors, in wound healing. *J Trauma* 1996; 41: 159-167). A review of multiple animal models for assessing efficacy of PDGF concluded that epithelialization and wound contraction were not significantly altered, whereas in most models, including the diabetic mouse model, granulation tissue thickness was consistently increased following application of the growth factor (LeGrand E K. Preclinical promise of Becaplermin (rhPDGF-BB) in wound healing. *Am J Surg* 1998; 176:48S-54S).

Similar improvements in wound healing appear to occur following application of NO, and this might be attributed to the inter-related mechanisms of action of NO with growth factors.

The significant increase in in vivo wound collagen deposition caused by treatment with NO indicates that delivery of NO from PVA hydrogel wound dressings may lead to the development of a more structurally stable closed wound. This finding is important, as chronic wounds are frequently complicated by their inability to remain healed due to insufficient mechanical integrity.

NO clearly plays a critical role in the wound healing process, most probably via multiple mechanisms including increased cell proliferation via upregulation of growth factor receptors and upregulation of matrix synthesis. That growth factors alone also enhance wound healing suggests that combining NO with growth factors may lead to synergistic effects.

Hydrogels may be modified to covalently attach growth factors, while maintaining the bioactivity of the growth factor (Mann B, Schmedlen R, West J. Tethered-TGF-beta increases extracellular matrix production of vascular smooth muscle cells. *Biomaterials* 2001; 22: 439-444). Thus, it is possible to develop hydrogels that provide combined NO and growth factor therapy to further enhance the healing of chronic wounds.

The materials described herein overcome some of the disadvantages of existing wound treatments by allowing the formation of hydrogel coatings through in situ polymerization. This technology may simplify the often difficult application of wound dressings to areas such as foot ulcers. Additionally, a multitude of factors to promote wound healing may be incorporated into these dressings through simple modification of the hydrogel material.

Treatment of Restenosis

A preferred application is a method of reducing the effects of restenosis on post-surgical patients. One embodiment of the method includes coating the surface within an artery with an aqueous solution of light-sensitive free radical polymerizable initiator and a number of macromers. The coated artery is subjected to a Xenon arc laser inducing polymerization of the macromers. As the newly polymerized macromer composition is formed, the physiological conditions within the artery will induce the release of NO. This release will be strictly localized for prolonged periods of time. In another embodiment of the method, a stent coated with the NO-releasing hydrogel is implanted in an artery.

Prevention of Surgical Adhesions.

A preferred application is a method of reducing formation of adhesions after a surgical procedure in a patient. In one embodiment the method includes coating damaged tissue surfaces in a patient with an aqueous solution of a light-sensitive free-radical polymerization initiator and a macromer solution as described above. The coated tissue surfaces are exposed to light sufficient to polymerize the macromer. The light-sensitive free-radical polymerization initiator may be a single compound (e.g., 2,2-dimethoxy-2-phenyl acetophenone) or a combination of a dye and a cocatalyst (e.g., ethyl eosin and triethanol amine).

Tissue Adhesives.

Another use of the polymers is in a method for adhering tissue surfaces in a patient. In one embodiment the macromer is mixed with a photoinitiator or photoinitiator/cocatalyst mixture to form an aqueous mixture and the mixture is applied to a tissue surface to which tissue adhesion is desired. The tissue surface is contacted with the tissue with which adhesion is desired, forming a tissue junction. The tissue junction is then irradiated until the macromers are polymerized.

Tissue Coatings.

In a particularly preferred application of these macromers, an ultrathin coating is applied to the surface of a tissue, most preferably the lumen of a tissue such as a blood vessel. One use of such a coating is in the treatment or prevention of restenosis, abrupt reclosure, or vasospasm after vascular intervention. An initiator is applied to the surface of the tissue, allowed to react, adsorb or bond to tissue, the unbound initiator is removed by dilution or rinsing, and the macromer solution is applied and polymerized. This method is capable of creating uniform polymeric coating of between one and 500 microns in thickness, most preferably about twenty microns, which does not evoke thrombosis or localized inflammation.

Tissue Supports.

The polymeric materials can also be used to create tissue supports by forming shaped articles within the body to serve a mechanical function. Such supports include, for example, sealants for bleeding organs, sealants for bone defects and space-fillers for vascular aneurisms. Further, such supports can include strictures to hold organs, vessels or tubes in a particular position for a controlled period of time.

Controlled Drug Delivery.

As noted above, the polymeric materials can be use as carriers for biologically active materials such as therapeutic, prophylactic or diagnostic agents, including hormones, enzymes, antibiotics, antineoplastic agents, and cell suspensions. The polymeric material may be used to temporarily preserve functional properties of an agent to be released, as well as provide prolonged, controlled release of the agent into local tissues or systemic circulation.

In a variation of the method for controlled drug delivery in which an agent is mixed with the macromer solution then polymerized in situ, the macromers are polymerized with the biologically active materials to form microspheres or nanoparticles containing the biologically active material. The macromer, photoinitiator, and agent to be encapsulated are mixed in an aqueous mixture. Particles of the mixture are formed using standard techniques, for example, by mixing in oil to form an emulsion, forming droplets in oil using a nozzle, or forming droplets in air using a nozzle. The suspension or droplets are irradiated with a light suitable for photopolymerization of the macromer.

These materials are particularly useful for controlled drug delivery of hydrophilic materials, since the water soluble regions of the polymer enable access of water to the materials entrapped within the polymer. Moreover, it is possible to polymerize the macromer composition containing the material to be entrapped without exposing the material to organic solvents. Release may occur by diffusion of the material from the polymer prior to degradation and/or by diffusion of the material from the polymer as it degrades, depending upon the characteristic pore sizes within the polymer, which is controlled by the molecular weight between crosslinks and the crosslink density. Deactivation of the entrapped material is reduced due to the immobilizing and protective effect of the gel and catastrophic burst effects associated with other controlled-release systems are avoided. When the entrapped material is an enzyme, the enzyme can be exposed to substrate while the enzyme is entrapped, provided the gel proportions are chosen to allow the substrate to permeate the gel. Degradation of the polymer facilitates eventual controlled release of free macromolecules in vivo by gradual hydrolysis of the terminal ester linkages.

As demonstrated by examples 1-3 below, three classes of NO-producing, PEG-based polymers have been synthesized and their NO release rate constants determined in vitro under physiological conditions. The biological response to appropriate materials has been evaluated in vitro using cultured smooth muscle cells and endothelial cells and in vivo using a rat carotid artery injury model that resembles restenosis in man. The materials include BAB block copolymers of polyethylene glycol (A) with polycysteine (B) that are subsequently reacted with $NaNO_2$ to form S-nitrosothiols, BAB block copolymers of polyethylene glycol ("PEG") (A) and diethylenetrianmine ("DETA") (B) that are subsequently reacted with NO gas to form nucleophile/NO complexes, and BAB block copolymers of polyethylene glycol (A) and polylysine (B) that are subsequently reacted with NO gas to form nucleophile/NO complexes. Blended compounds may also be prepared for providing biphasic release of profiles, such as PEG-Cys-DETA-NO. All polymers are further terminated with reactive acrylate groups to allow rapid polymerization in situ.

Such materials would be expected to have good biocompatibility, provided that a water soluble, biocompatible polymer such as PEG comprises the bulk of the material and has a sufficiently high molecular weight, and to slowly biodegrade due to the presence of two ester bonds and two amide bonds in each polymer chain. These three materials were selected as they are expected to have vastly different release kinetics: nucleophile/NO complexes have been shown to release NO for up to 5 weeks (Smith el al., (1996) *J. Med. Chem.*, 39:1148-56), while the half-life of S-nitrosocysteine is 0.023 hours (Mathews et al., (1993) *J. Pharmacol. Exp. Therap.*, 267:1529-37). The amount of NO produced by these copolymers may be tailored by altering the ratio of polyethylene glycol (PEG) to cysteine or lysine.

An advantage of these macromer compositions are that they can be polymerized rapidly in an aqueous surrounding. Precisely conforming, semi-permeable, biodegradable films or membranes can thus be formed on tissue in situ to serve as biodegradable barriers, as carriers for living cells or other biologically active materials, and as surgical adhesives. The polymer shows excellent biocompatibility, as seen by a minimal fibrous overgrowth on implanted samples. Hydrogels for the models were gelled in situ from water-soluble precursors by brief exposure to LWUV light, resulting in formation of an interpenetrating network of the hydrogel with the protein and glycosaninoglycan components of the tissue.

As demonstrated by examples 4 and 5 below, three types of PVA hydrogels were made and demonstrated release of NO and incorporated drug (bFGF): PVA-$NH_2$-NO hydrogels; PVA-Cys-NO hydrogels; PVA-NO-bFGF hydrogels. The results are similar to those for the PEG based hydrogels.

The invention will be described in greater detail by way of specific examples. The following examples are offered for illustrative purposes, and are intended neither to limit nor define the invention in any manner.

EXAMPLES

Example 1

Synthesis of PEG-Cys-NO Macromers and Hydrogels

As shown in FIG. 1, an acryloyl-PEG-Cys-NO polymer was formed by first reacting polyethylene glycol N-hydroxysuccinimide monoacrylate (ACRL-PEG-NHS, MW 3400, commercially available from Shearwater Polymers, Huntington, Ala.) with L-cysteine at an 1:2 molar ratio in 50 mM sodium bicarbonate buffer (pH 8.5) for 2 hours; the product was then dialyzed in a cellulose ester membrane (Molecular weight cutoff 500, Spectrum Labs, Laguna Hills, Calif.) in di$H_2O$, and lyophilized. Analysis of the acryloyl-PEG-Cys copolymer was performed using gel permeation chromatography (GPC) with an evaporative light scattering detector and a UV detector at 260 nm (Polymer Laboratories, Amherst, Mass.). Successful synthesis of acryloyl-PEG-Cys was determined by a shift in the position of the peak from the evaporative light scattering detector. The copolymer was then reacted with an equimolar amount of $NaNO_2$ at pH 2 and 37° C. for 20 minutes to form S-nitrosocysteine. Conversion of thiol groups to S-nitrosothiols was measured using the Ellman's assay (Hermanson, (1995) *Bioconjugate Techniques*, San Diego, Calif. Academic Press; 88-90). After adjusting the pH of the solution to 7.4, the acryloyl-PEG-Cys-NO polymer was incorporated into photopolymerizable hydrogels by mixing with PEG-diacrylate (MW 3400) at a 1:10 molar ratio in aqueous solution with 1500 ppm 2,2-dimethoxy-2-phenyl acetophenone as a long wavelength ultraviolet initiator. 0.15% N-vinylpyrrolidone was present in this mixture as it was used as a solvent for the photoinitiator. Exposure to UV light (365 nm, 10 mW/$cm^2$) was used to crosslink the polymer, resulting in conversion to a hydrogel (Sawhney et al., (1993) *Macromol* 26:581-7).

Example 2

Synthesis of PEG-$Lys_5$-NO Macromers and Hydrogels

Figure 2:
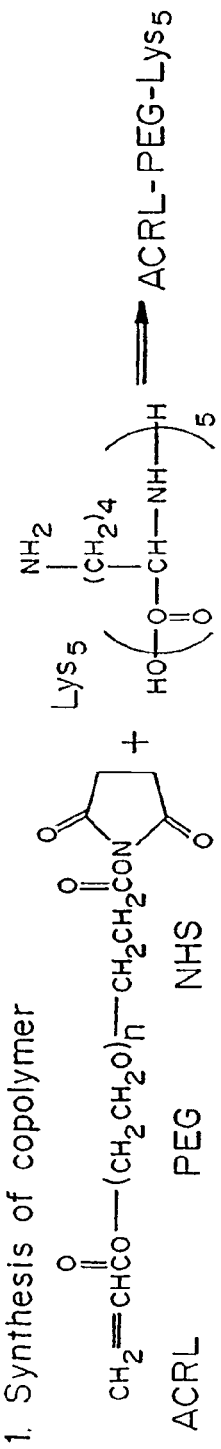
FIG. 2 is a schematic of the synthesis of acryloyl-PEG-Lysine$_5$ NO-nucleophile complex hydrogels.
Figure 2:
Figure 2:
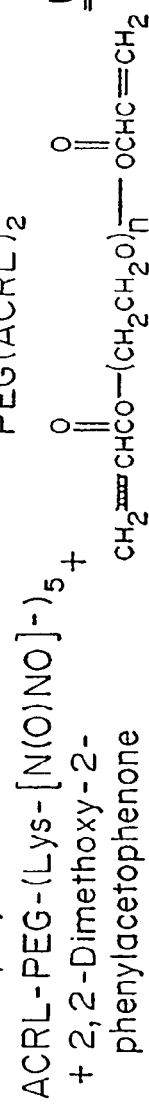
Figure 2:

As shown in FIG. 2, for acryloyl-PEG-$Lys_5$-NO hydrogels, a copolymer of ACRL-PEG-NHS (MW 3400, Shearwater Polymers) and poly-L-lysine (DP=5) was synthesized by reacting at an equimolar ratio in 50 mM sodium bicarbonate (pH 8.5). The resultant copolymer was analyzed via GPC, then dissolved in water and reacted with NO gas in an evacuated vessel, thus forming NO-nucleophile complexes with the amine groups on the lysine side groups. The extent of conversion of amine groups to NO-nucleophile complexes was measured using the ninhydrin assay, and crosslinked hydrogels were formed as described above in Example 1.

Example 3

Synthesis of PEG-DETA-NO Macromers and Hydrogels

Figure 3:
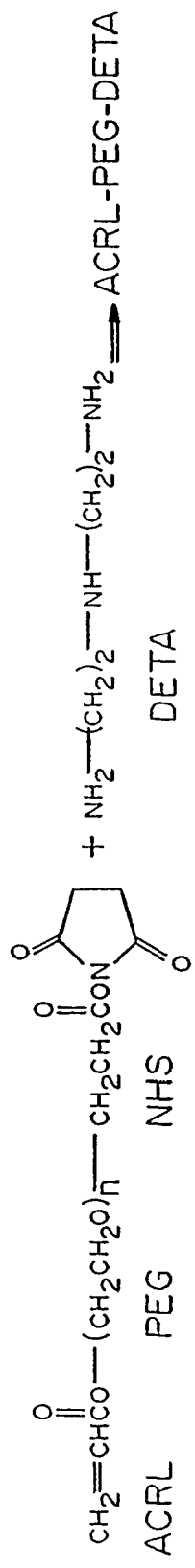
FIG. 3 is a schematic of the synthesis of acryloyl-PEG-DETA-NO-nucleophile complex hydrogels.
Figure 3:
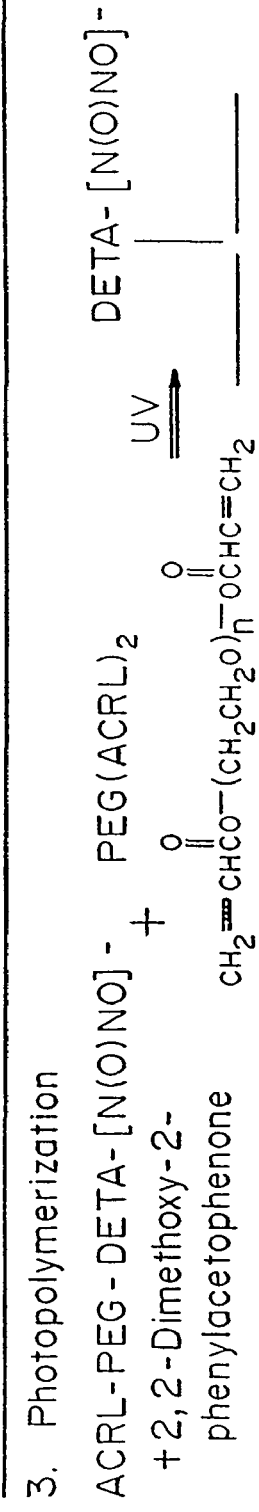

Diethylenetriamine (DETA, Aldrich, Milwaukee; Wis.) was reacted with ACRL-PEG-NHS (MW 3400, Shearwater Polymers) in 50 mM sodium bicarbonate buffer (H 8.5) at an equimolar ratio, lyophilized, and analyzed via GPC as described above. The copolymer was then dissolved in water and exposed to NO gas to form NO-nucleophile complexes as described for PEG-$Lys_5$-NO and assayed for amine content using the ninhydrin assay. The PEG-DETA-NO was lyophilized and then photopolymerized as described above to form hydrogels, as shown in FIG. 3.

Example 4

Synthesis of PVA-$NH_2$-NO Macromers and Hydrogels

Poly(vinyl alcohol) (Hoechst, Mowiol 4-88) was dissolved in di$H_2O$ and warmed to 95° C. in a round bottom flask under continuous stirring. After one hour, the solution was cooled to room temperature, and a crosslinkable acetal group, methacrylamidoacetaldehyde dimethyl acetal (NAAADA) was added. The amine acetal, gamma-aminobutyraldehyde diethyl acetal, was also added, and the mixture was acidified using glacial acetic acid and 37% hydrochloric acid. The mixture was allowed to stir at room temperature for nine hours, after which the pH was adjusted to pH 3.6 using triethylarnine. In order to purify the polymer, the solution was then diafiltered through a MW 3000 cellulose membrane against di$H_2O$ at 6.5 times the volume of polymer solution. The polymer concentration was adjusted to 22% w/v using diafiltration, and the pH was adjusted to 7.4 with 1N NaOH. The amine concentration of the polymer was determined using the ninhydrin assay.

In order to form the NO donor bound to the PVA-$NH_2$, the neutralized amine-modified polymer was placed in a round bottom flask with stopcock. The flask was evacuated and filled with nitric oxide gas until the desired conversion of amines to NO nucleophile complexes was achieved. Photocrosslinked hydrogels were formed from the PVA-$NH_2$-NO by adding 0.1% IRGACURE™ 2959 (Ciba-Geigy) photoinitiator (based on total solution volume) and then exposing to UV light (2 mW/$cm^2$, 365 nm) for 30 seconds. Addition of the photoinitiator brings the final polymer concentration to 20% w/v.

Example 5

Synthesis of PVA-Cys-NO Macromers and Hydrogels

PVA-$NH_2$ was synthesized as described above. The amine terminus of cysteine was acetylated using acetic anhydride, and the carboxyl end of the cysteine was coupled to the PVA-$NH_2$ using water-soluble EDAC chemistry. The resulting PVA-Cys was then purified using diafiltration and brought to a concentration of 22% w/v. PVA-Cys-NO was formed by adding sodium nitrite at an equimolar amount to cysteine residues, adjusting the pH to 2, and incubating at 37° C. for 15 minutes. The extent of reaction of cysteine to Cys-NO was assayed using both the Ellman's and Griess reactions. The photoihitiator, 2,2-methyl-2-phenylacetophenone was dissolved in N-vinylpyrrolidone at a concentration of 600 mg/ml and added to the polymer solution (0.1% based on total solution volume). The polymer was then crosslinked under UV light for 30 seconds and placed in HEPES buffered saline, pH 7.4, 37° C.

Example 6

Synthesis of PVA-NO-BFGF Hydrogels

For PVA-NO-bFGF hydrogels, the above procedure was used to make the PVA-NO polymer. Immediately prior to exposure to UV light, 25 μg/ml bFGF was added to the polymer solution and mixed well. Gels were crosslinked as described earlier and stored in HEPES buffered saline, pH 7.4, 37° C.

Example 7

NO Release From Hydrogels

Following preparation and polymerization of the NO-releasing materials as described above, the hydrogels were weighed and stored in HEPES buffered saline, pH 7.4, at 37° C. Aliquots of the buffer were removed at each time point and replaced with fresh buffer. The samples from each time point were then analyzed for nitrite content using a colorimetric assay based on the Griess reaction.

NO release kinetics of hydrogels stored in buffer at various pH levels were also investigated in order to explore possible storage conditions for the hydrogels. At acidic pH levels, release of NO from the hydrogels was significantly inhibited.

Figure 4:
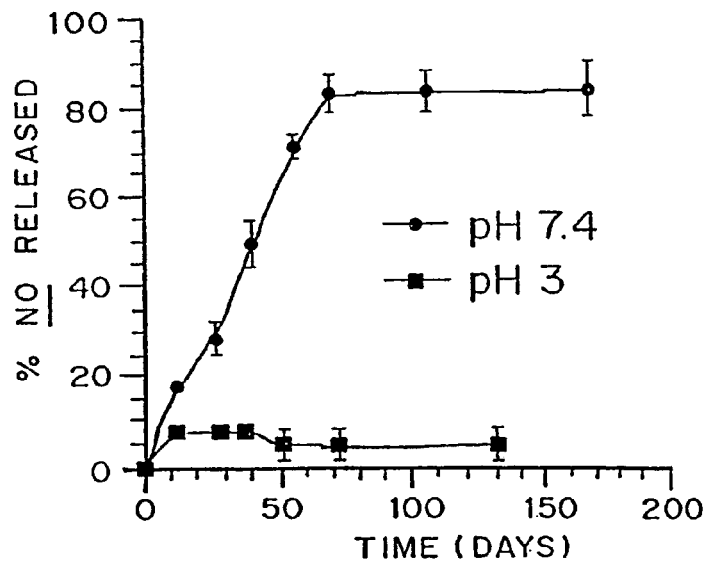
FIG. 4 is a graph showing the temporal release (% NO released over time in days) of NO from acryloyl-PEG-Lys$_5$-NO hydrogels at pH 7.4 (circles) and pH 3 (squares).

NO release from acryloyl-PEG-Lys$_5$-NO hydrogels is shown in FIG. 4.

Figure 5:
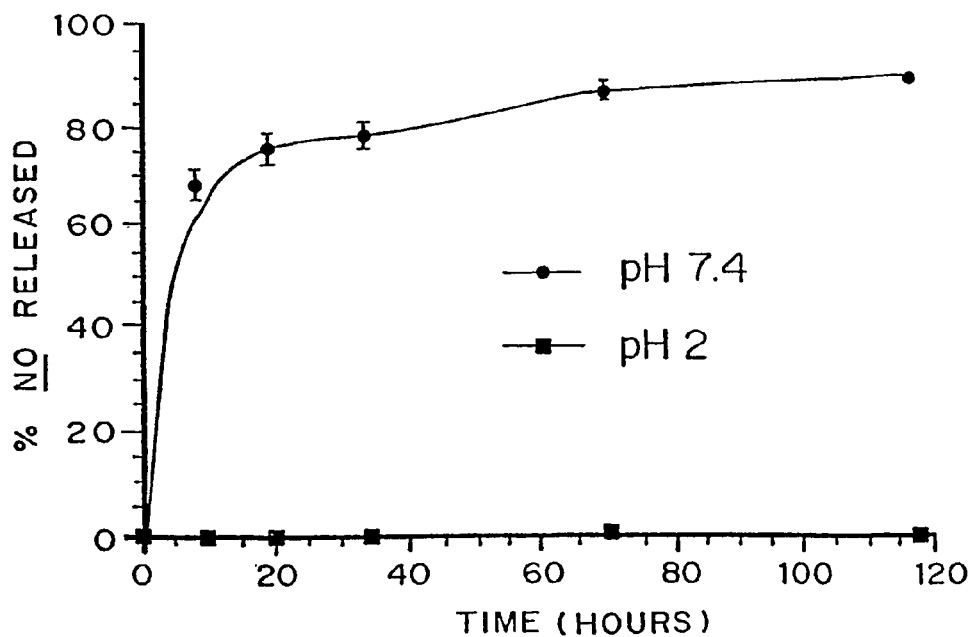
FIG. 5 is a graph showing the temporal release (% NO released over time in hours) of NO from acryloyl-PEG-DETA-NO hydrogels at pH 7.4 (circles) and pH 2 (squares).

NO release from acryloyl-PEG-DETA-NO hydrogels is shown in FIG. 5.

Figure 6:
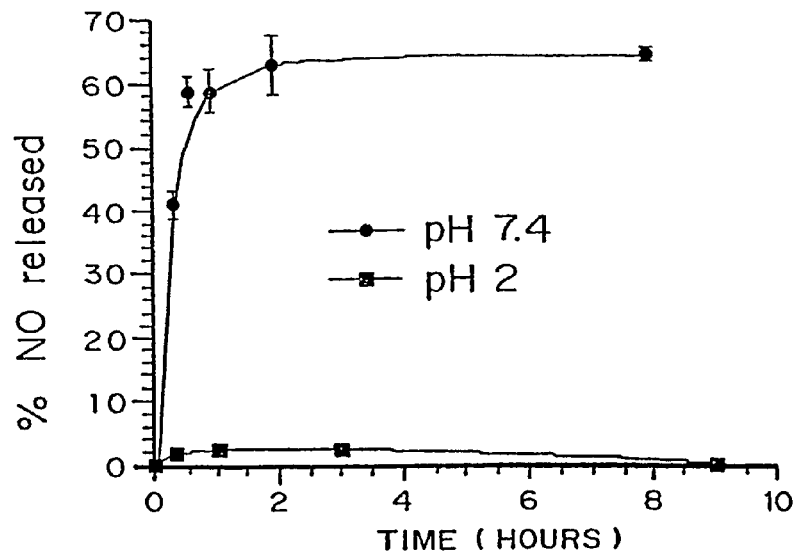
FIG. 6 is a graph showing the temporal release (% NO released over time in hours) of NO from PEG-Cys-NO hydrogels at pH 7.4 (circles) and pH 2 (squares).

NO release from acryloyl-PEG-Cys-NO hydrogels is shown in FIG. 6.

Example 8

NO and BFGF Release from PVA-NO-BFGF Hydrogels

Figure 7A:
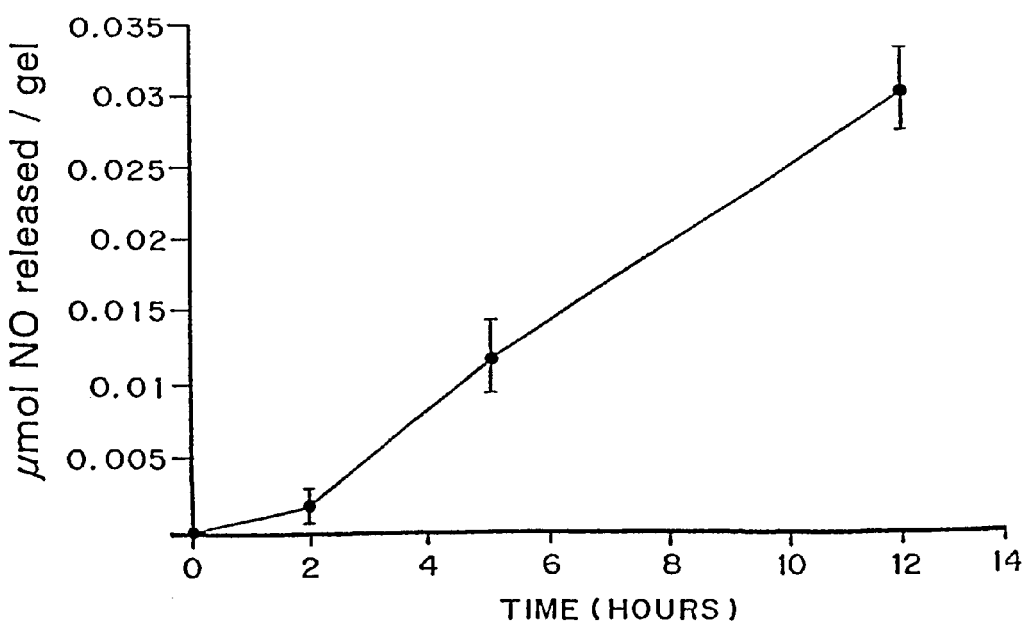
FIG. 7A is a graph showing the temporal release (μmol NO released per gram of polymer over time in hours) of NO from PVA-NO-bFGF hydrogels at pH 7.4, 37° C.
Figure 7B:
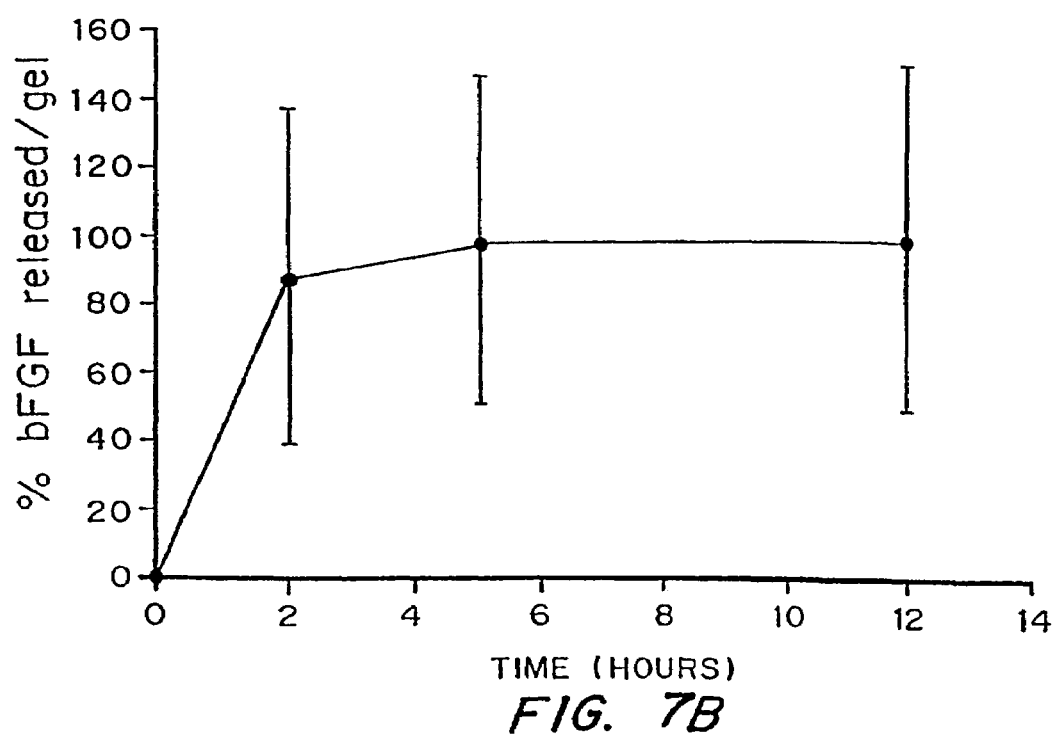
FIG. 7B is a graph showing the temporal release (% of theoretical bFGF released per gram of gel over time in hours) from PVA-NO-bFGF hydrogels at pH 7.4, 37° C.

The release of NO release from PVA-NO-bFGF hydrogels prepared as described in Example 6 was determined in the same manner as Example 7 and is shown in FIG. 7A. Release of bFGF was quantified using that BCA assay (Pierce Chemicals) and is shown in FIG. 7B. Release of NO continues for well over 12 hours, while the growth factor is completely released within the first 5 hours.

Example 9

Effects of NO-Releasing Macromers on Cultured Smooth Muscle Cells: Profileration and Viability In order to assess the potential of a material for the reduction of smooth muscle cell proliferation after vascular injury, cultured smooth muscle cells were grown in the presence of NO-releasing materials, and the effects of those materials on the cells evaluated. Smooth muscle cells isolated from Wistar-Kyoto rats (passage 11-15, provided by T. Scott-Burden) were cultured in Minimum Essential Medium supplemented with 10% FBS, 2 mM L-glutamnine, 500 units penicillin, and 100 mg/L streptomycin, at 37° C. in a 5% $CO_2$ environment. The cells were seeded into 24-well tissue culture plates (Becton Dickinson, Franklin Lakes, N.J.) at a density of 10,000 cells/cm$^2$. NO donors in either soluble or hydrogel form were added to the media in the wells one day after seeding. At 4 days culture, cell numbers were determined by preparing single cell suspensions with trypsin and counting three samples from each group using a Coulter counter (Multisizer #0646, Coulter Electronics, Hialeah, Fla.).

The effects of NO donors in solution on the proliferation of smooth muscle cells were first investigated by performing a NO dose response curve, whereupon cells were cultured with a range of NO donor concentrations (1 μM-10 mM) in order to identify appropriate dosages for hydrogel studies. NO-nucleophile complexes (Lys-NO and DETA-NO) were formed by reacting either L-lysine or DETA with NO gas in water for 24 hours. Soluble Cys-NO was synthesized by reacting an equimolar amount of L-cysteine with $NaNO_2$ at pH 2 and 37° C. for 20 minutes. All NO donor solutions were adjusted to pH 7.4 prior to addition to cell cultures.

Smooth muscle cell proliferation in the presence of NO-producing and control hydrogels was then investigated using the optimal NO dose determined above. Hydrogels containing acryloyl-PEG-Lys$_5$-NO, acryloyl-PEG-DETA-NO, and acryloyl-PEG-Cys-NO were formed as described above, except that the gel solutions were sterile filtered through 0.2 μm syringe filters (Geiman Sciences, Ann Arbor, Mich.) prior to adding 2,2-dimethoxy-2-phenyl acetophenone. PEG-diacrylate hydrogels containing no NO donors were used as a control. The hydrogels were photopolymerized in cell culture inserts (8 μm pore size, Becton Dickinson, Franklin Lakes, N.J.) and placed in the media over the cultured cells.

All three hydrogel NO donors significantly inhibited SMC growth ($p<0.0001$). The number of smooth muscle cells remained near that of the seeding density, which ranged from 10-15% of the final control cell number for all experiments.

Figure 8A:
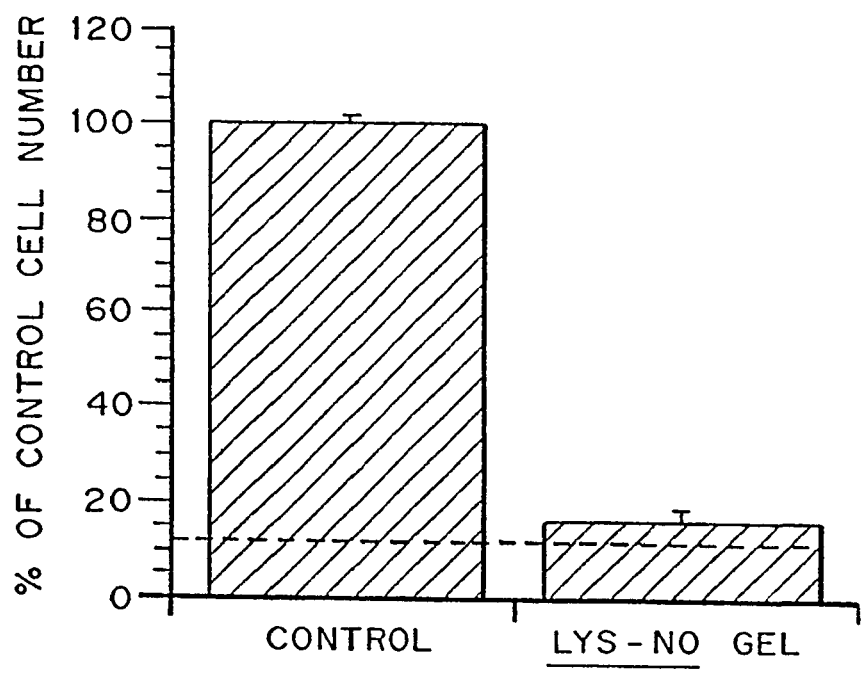
FIGS. 8A and 8B are graphs showing that acryloyl-PEG-Lysine-NO hydrogels inhibit the proliferation of smooth muscle cells.
Figure 8B:
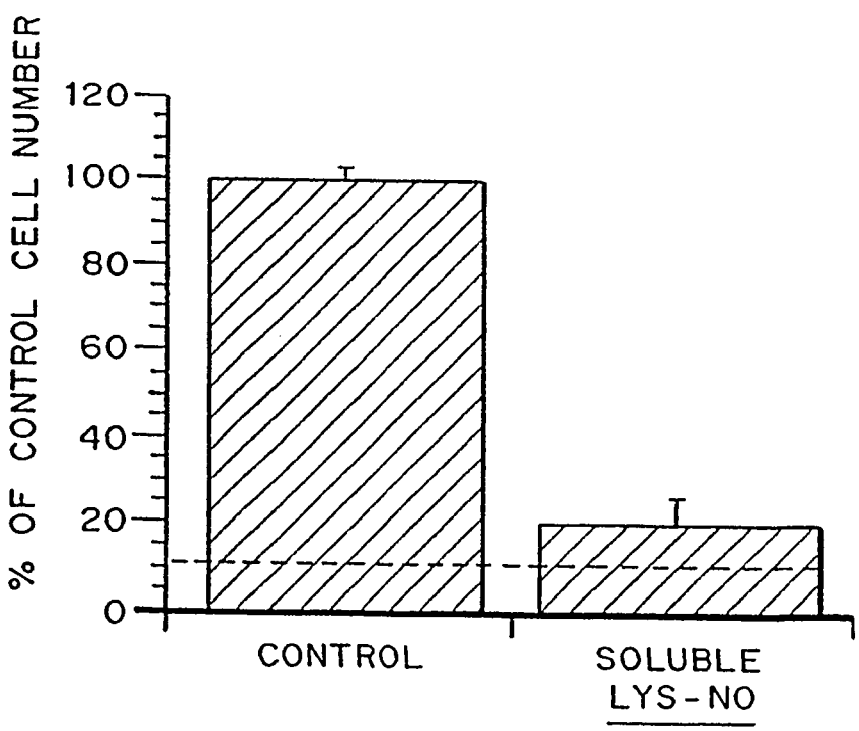

Inhibition of SMC proliferation by acryloyl-PEG-Lys$_5$-NO hydrogels is shown in FIG. 8A, compared to the macromer solution control shown in FIG. 8B. Both significantly inhibited SMC proliferation.

Figure 9A:
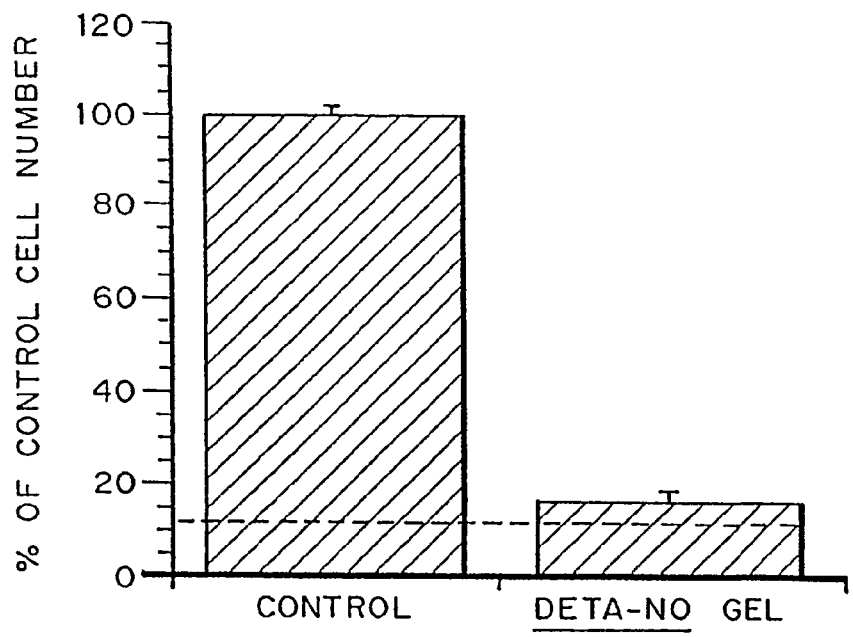
FIGS. 9A and 9B are graphs showing the inhibition of SMC proliferation by NO released from acryloyl-PEG-DETA-NO hydrogels (FIG. 9A) and soluble polymer (FIG. 9B), as a percentage of the control.
Figure 9B:
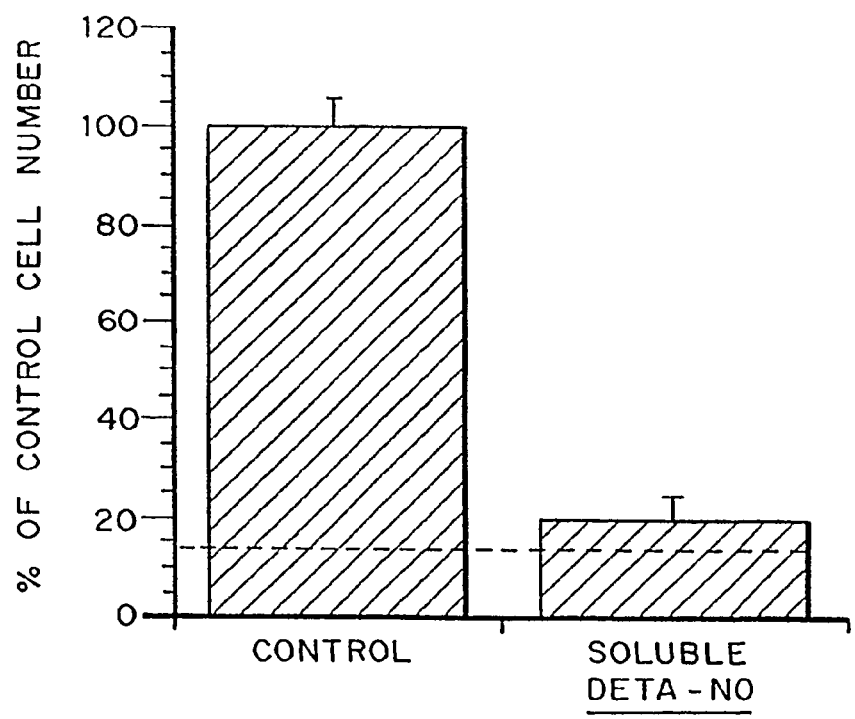

Inhibition of SMC proliferation by acryloyl-PEG-DETA-NO-nucleophile complex hydrogels is shown in FIG. 9A, compared to the macromer solution control shown in FIG. 9B. Both significantly inhibited SMC proliferation.

Figure 10A:
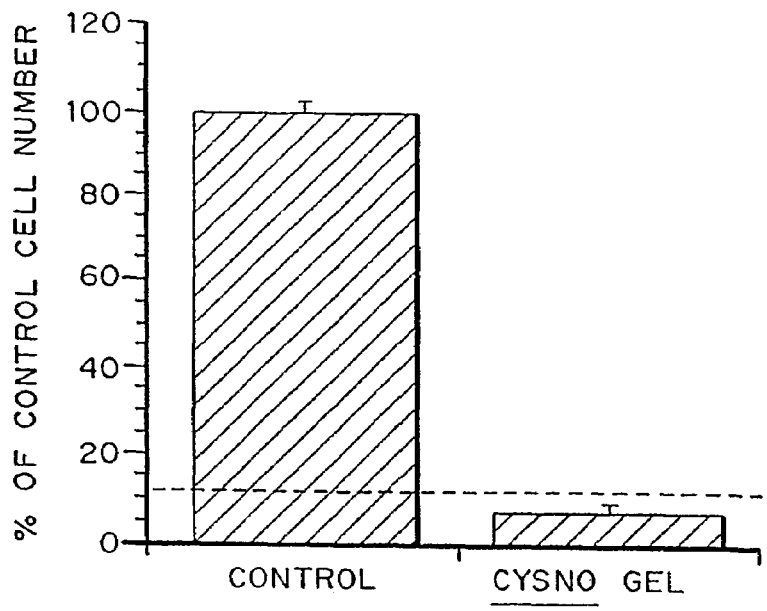
FIGS. 10A and 10B are graphs showing inhibition of SMC proliferation by NO released from acryloyl-PEG-Cys-NO hydrogels (FIG. 10A) and soluble polymer (FIG. 10B), as a percentage of controls.
Figure 10B:
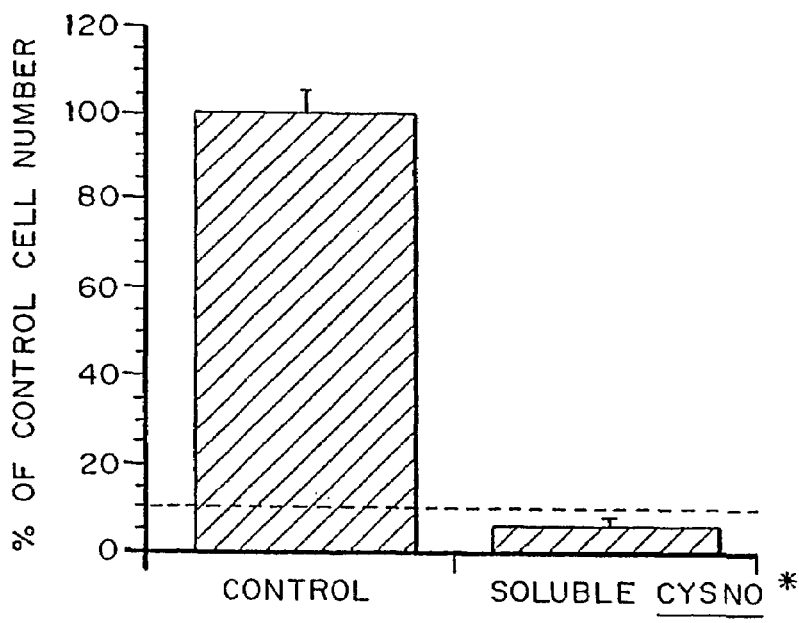

Inhibition of SMC proliferation by acryloyl-PEG-Cys-NO hydrogels is shown in FIG. 10A, compared to the macromer solution control shown in FIG. 10B. Both significantly inhibited SMC proliferation.

Figure 11:
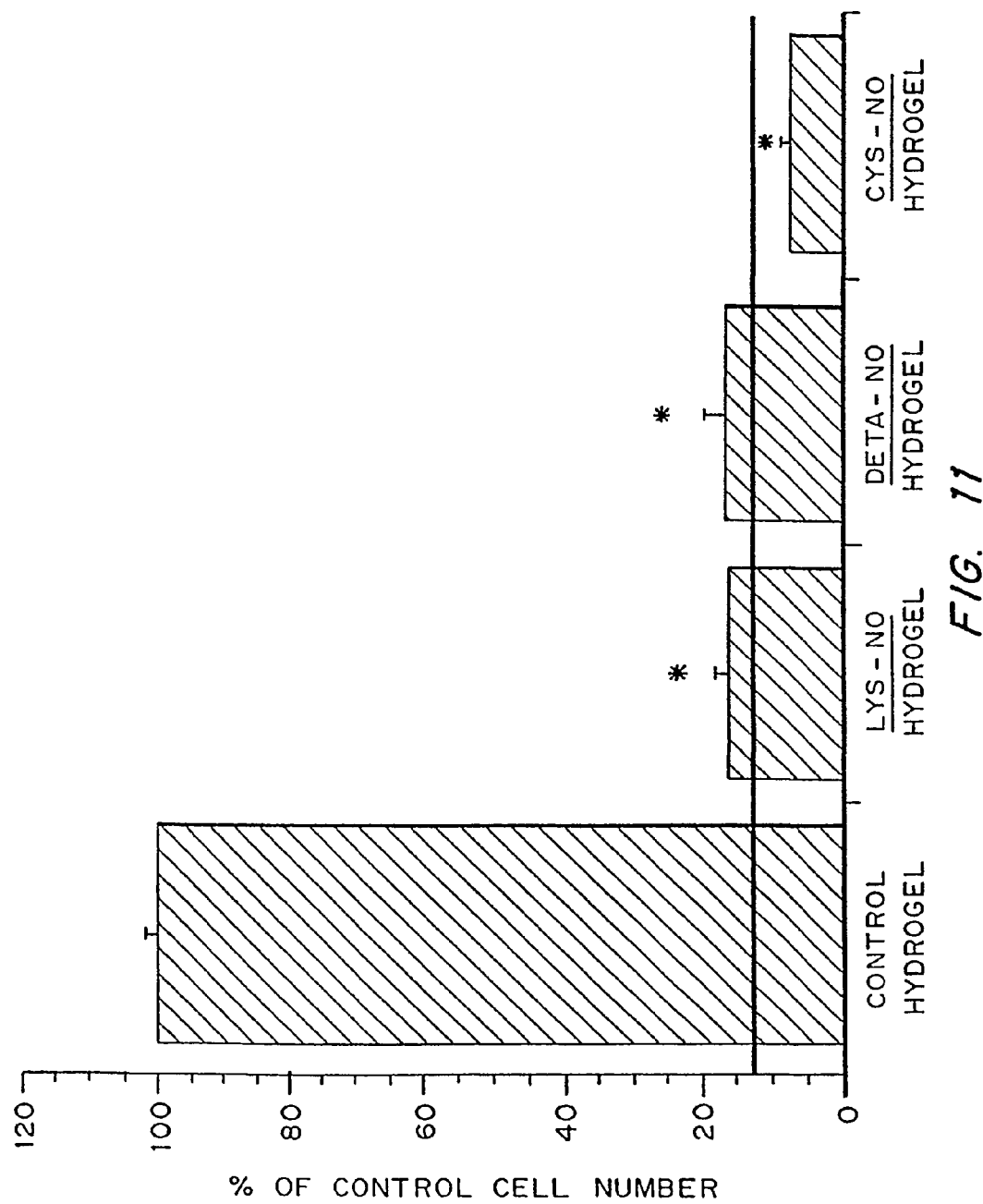
FIG. 11 is a graph comparing the degree of inhibition of smooth muscle cell growth by NO released from hydrogels: acryloyl-PEG-Lys-NO, acryloyl-PEG-DETA-NO, and acryloyl-PEG-Cys-NO, compared to control hydrogel with NO. The percent inhibition of smooth muscle cell growth is determined by comparing the cell growth for each NO-releasing hydrogel to a control PEG-diacrylate hydrogel.

Inhibition of SMC proliferation by acryloyl-PEG-Cys-NO hydrogels, acryloyl-PEG-DETA-NO hydrogels, and acryloyl-PEG-Lys-NO hydrogels is compared to the control hydrogel in FIG. 11. All of the NO hydrogels significantly inhibited SMC growth.

Example 10

Effects of NO-Releasing Macromers on Platelet Adhesion In Vitro

The effect of NO release on platelet adhesion was investigated to assess the potential of these materials for prevention of thrombosis. Blood was obtained from a healthy volunteer by venipuncture and anticoagulated with 10 U/ml heparin. Platelets and white blood cells were fluorescently labeled with mepacrine at a concentration of 10 μM. A solution of 2.5 mg/ml collagen I in 3% glacial acetic acid in $diH_2O$ was prepared and applied to glass slides for 45 minutes in a humidified environment at room temperature. Acryloyl-PEG-Cys-NO and PEG-diacrylate hydrogels were prepared as described above and incubated with the labeled whole blood at 37° C. for 30 minutes. The hydrogels were removed and the blood was then incubated with the collagen-coated glass slides (two per group) for 20 minutes at 37° C. and then rinsed with HBS. Platelet counts per field of view at 40× were counted under a fluorescent microscope (Zeiss Axiovert 135, Thornwood, N.Y.) in four randomly chosen areas per slide.

Photos of platelets which had been exposed to control PEG-diacrylate or acryloyl-PEG-Cys-NO hydrogels demonstrate that exposure to the NO-releasing hydrogels inhibits platelet adhesion to thrombogenic surfaces. Glass slides coated with collagen were used as a thrombogenic surface to which platelets would normally adhere. When the blood was incubated with control PEG-diacrylate hydrogels, 69.25±4.46 (mean±SD) adherent platelets were observed per field of view. This number was reduced to 7.65±6.16 platelets pre field of view when blood was pre-exposed to the acryloyl-PEG-Cys-NO hydrogels ($p<0.0001$).

Example 11

Effects of NO-Releasing Macromers on Cultured Endothelial Cells: Proliferation and Viability The polymeric materials described herein can be used to increase proliferation of endothelial cells.

Cell Viability

Bovine aortic endothelial cells (BAECs, passage 5-10, Clonetics) were cultured in Dulbecco's Modified Eagle Medium with identical supplements and culture conditions to the smooth muscle cells. The viability of endothelial cells exposed to NO-releasing PEG gels was examined through the use of a Live/Dead staining kit (Molecular Probes, Eugene, Oreg.). BAECs were seeded into 24-well plates at a concentration of 10,000 cells/$cm^2$, and hydrogels were added as described above. After two days in culture, cell viability was assessed. As discussed earlier, a 4 µM solution of ethidium bromide causes dead cells to fluoresce red due to their increased permeability, while a 2 µM solution of calcein AM causes viable cells to fluoresce green due to esterase activity. Cells were examined under a fluorescence microscope (Zeiss Axiovert 135, Thornwood, N.Y.), and photomicrographs were taken using a digital camera (Sony).

Endothelial Cell Proliferation

BAECs cells were seeded into 24-well tissue culture plates (Becton Dickinson, Franklin Lakes, N.J.) at a density of 10,000 cells/$cm^2$. NO donors in soluble form (1 µM-10 mM) were added to the media in the wells one day after seeding. After 4 days of culture, cell numbers were determined by preparing single cell suspensions with trypsin and counting three samples from each group using a Coulter Counter (Multisizer #0646, Coulter Electronics, Hialeah, Fla.).

Endothelial cell proliferation in the presence of NO-producing and control hydrogels was then investigated using the optimal NO dose determined above. After four days in culture with the hydrogels, cell numbers were detemined by preparing single cell suspensions with trypsin and counting three samples from each group using a Coulter Counter as described above.

Endothelial Cell Proliferation on NO-releasing Hydrogels

In order for these hydrogels to effectively prevent restenosis, re-endothelialization must occur not only in areas surrounding the hydrogel, but also upon the hydrogel itself. To investigate the proliferation of endothelial cells cultured on NO-releasing hydrogels, a cell adhesion ligand was first covalently incorporated into these hydrogels, as cells will not attach to PEG unless the polymer is modified with an adhesive sequence (Hern D, Hubbell J. Incorporation of adhesion peptides into nonadhesive hydrogels useful for tissue resurfacing, *J Biomed Mater Res* 1998; 39: 266-276). To achieve this, hydrogels containing the adhesive peptide sequence RGDS (Arginine-Glycine-Aspartic acid-Serine) and the NO donor DETA-NO were synthesized. RGDS was covalently bound to PEG by reaction with ACRL-PEG-NHS in a ratio of 1:2 (RGDS:polymer) in 50 mM sodium bicarbonate buffer (pH 8.5) for two hours at room temperature. The solution was then dialyzed and lyophilized to obtain ACRL-PEG-RGDS. ACRL-PEG-DETA-NO was prepared as described above. These two copolymers were blended with PEG-diacrylate to achieve a final RGDS concentration of 1.4 µmol/ml of polymer, and 1.25 µmol DETA-NO/ml of polymer, which would theoretically deliver a total of 50 nmol NO donor per ml of cell culture media. The hydrogel precursor solution was filter sterilized and poured between two polystyrene plates separated by a 400 µm gap. The hydrogel precursor was exposed to UV light, and a sterilized cork-borer punch (Cole Parmner, Vernon Hills, Ill.) was used to create thin, circular hydrogels that were subsequently placed in a 24-well plate. BAECs were immediately seeded upon the hydrogels at a density of 7500 cells/$cm^2$. Controls consisted of hydrogels with the NO donor alone or RGDS alone. Two days after cell seeding, cells were trypsinized and cell number was assessed by counting on a Coulter Counter.

Hydrogels containing the cell adhesive ligand REDV were also prepared. Synthesis of acryloyl-PEG-REDV was identical to the synthesis of acryloyl-PEG-RGDS except that the concentration of REDV in the hydrogels was 14 µmol/ml. Endothelial cell seeding experiments were also identical.

Results: Cell Proliferation and Viability

Figure 12:
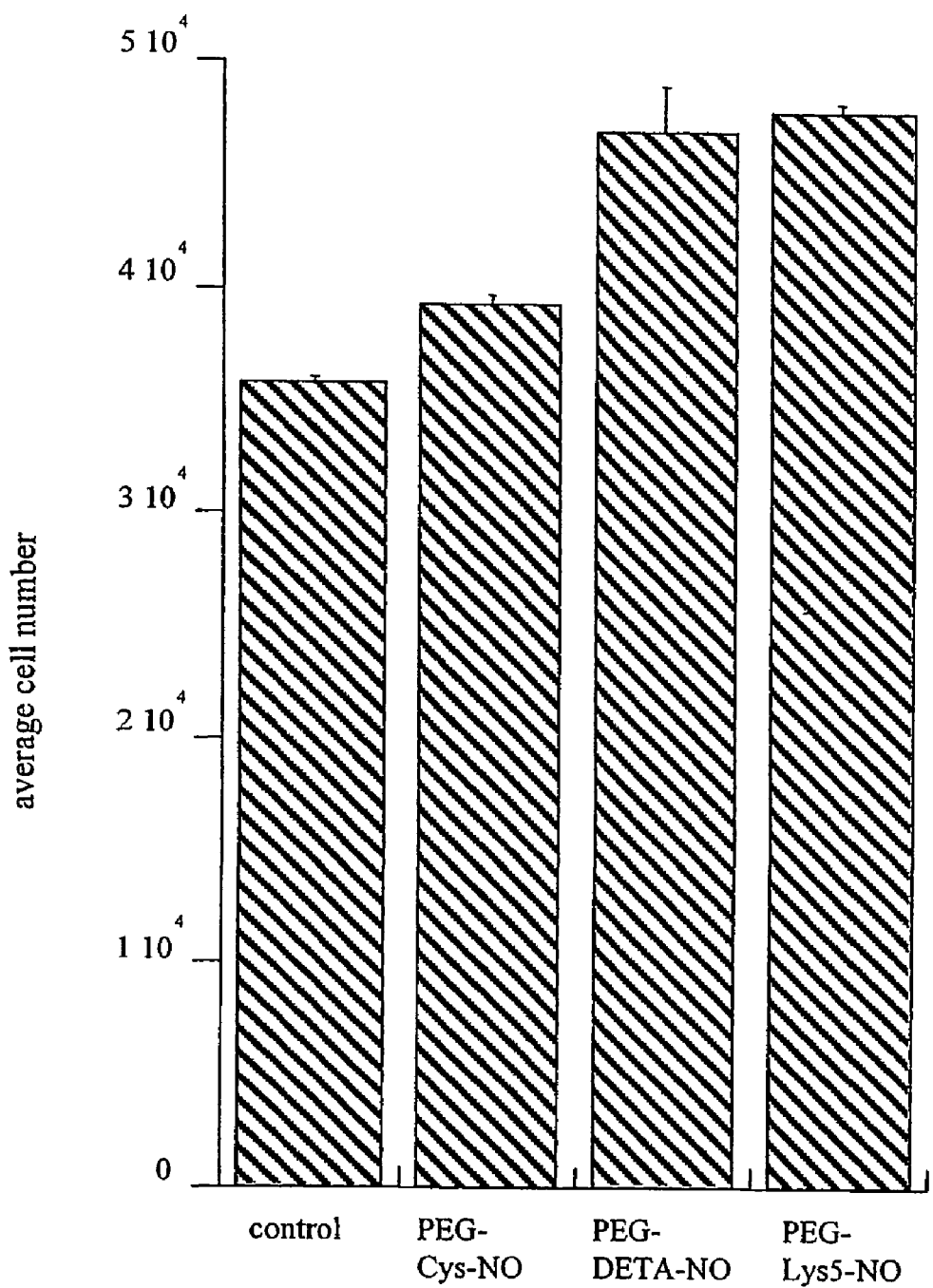
FIG. 12 is a graph of endothelial cell proliferation, which was stimulated when cultured in the presence of NO-releasing PEG hydrogels with varying NO release kinetics. PEG-diacrylate hydrogels were used as a control. The last three bars represent a statistical variance of $p \leq 0.01$ compared to control.

The effects of NO release from these hydrogel materials on endothelial cell proliferation was investigated in order to examine whether NO delivery would have a stimulatory effect on re-endothelialization following vascular injury. A concentration of 0.5 µmoles NO released in 1 ml media (0.5 mM) over the course of the experiment was chosen as the optimal NO concentration from studies performed with a range of soluble NO donor concentrations; this concentration resulted in increased proliferation of endothelial cells. At lower concentrations of NO (50 µM-0.1 mM), endothelial cell proliferation was still significantly increased, while concentrations greater than 1 mM resulted in a decrease in cell number. All three hydrogel NO donors significantly increased endothelial cell growth with no change in cell viability (FIG. 12), indicating that release of NO from PEG hydrogels may lead to faster re-endothelialization of vessels following injury, which would be beneficial in preventing restenosis.

Endothelial Cell Proliferation on NO-releasing Hydrogels

Figure 13:
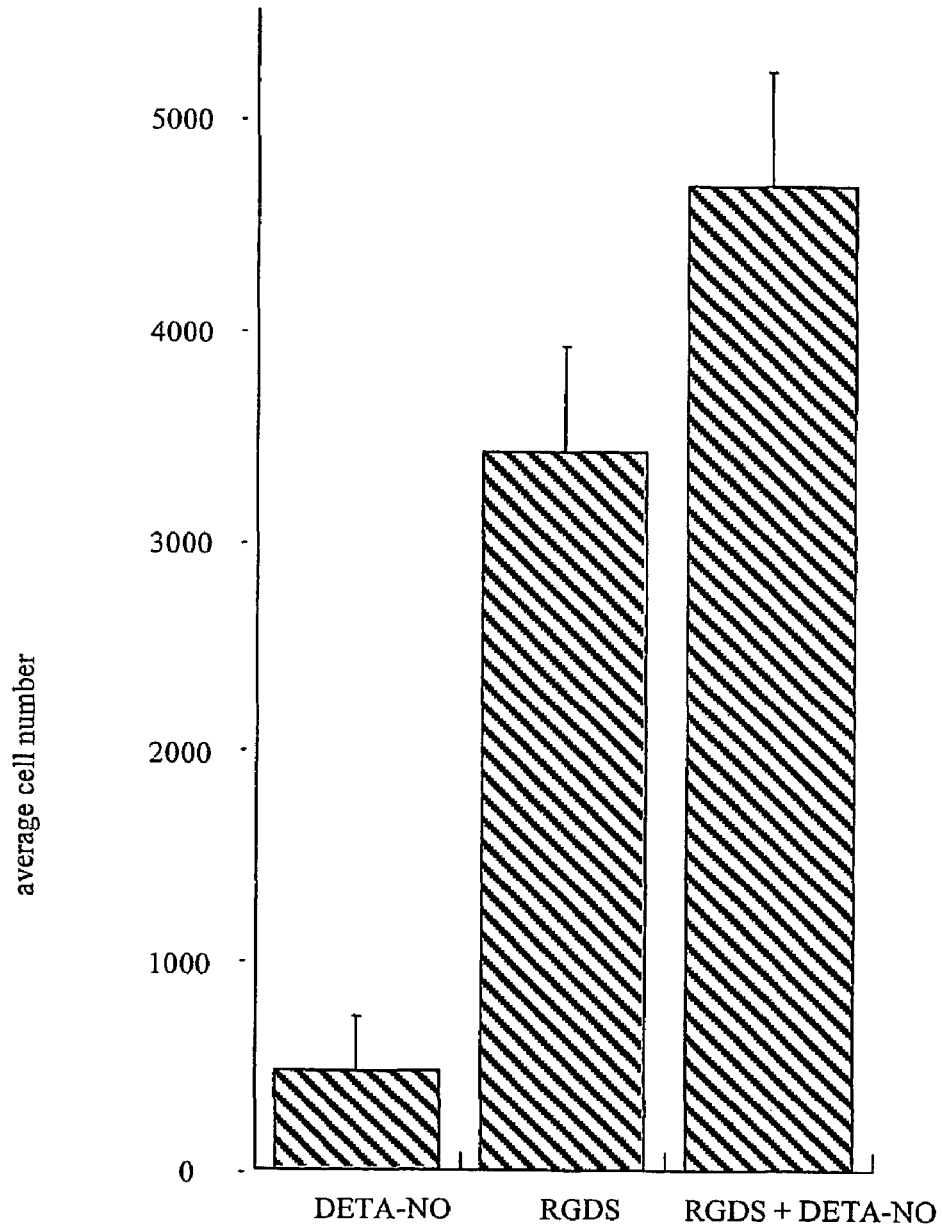
FIG. 13 is a graph of endothelial cell proliferation, which was stimulated when cultured on NO-releasing hydrogels that contained the cell adhesion peptide sequence RGDS. The last bar represents a statistical variance of $p<0.02$ versus either RGDS or DETA-NO hydrogels alone.

Hydrogels were synthesized with the covalently bound adhesive peptide sequence RGDS in addition to the NO donor DETA-NO in order to examine endothelial cell proliferation when cultured on NO-releasing hydrogels. After two days in culture, there were significantly more cells on the hydrogels containing both RGDS and DETA-NO than on either of the control materials (FIG. 13). As expected, very few cells were adhered to the hydrogels containing DETA-NO with no peptide sequence. While cells attached and proliferated on the hydrogels containing RGDS but no NO donor, the combination of the NO donor with the peptide sequence allowed for increased proliferation over the peptide alone. These findings further illustrate the ability of NO to stimulate endothelial cell proliferation. Additionally, this experiment demonstrates that molecules such as peptide sequences may also be covalently bound to NO-releasing hydrogels in order to design a material that further encourages re-endothelialization. Potential applications for these materials are not limited to the prevention of restenosis, as they may also be used to coat blood-contacting devices such as stents or vascular grafts where enhanced endothelialization is desirable.

Endothelial Cell Proliferation Employing Cell Adhesion Ligand REDV

Figure 14:
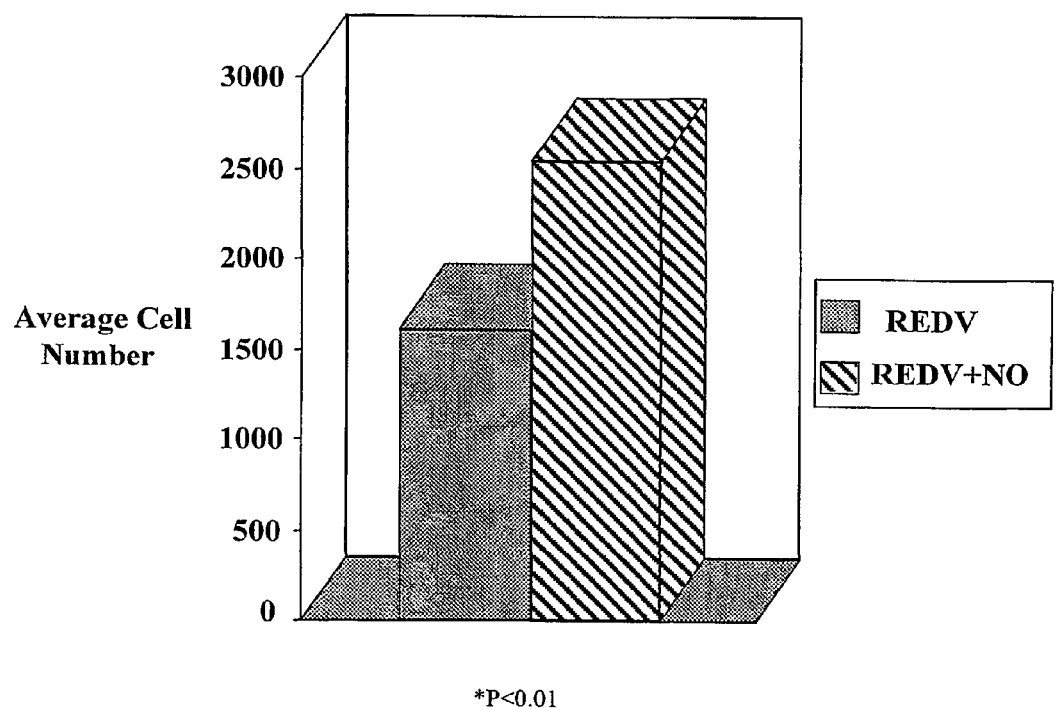
FIG. 14 is a graph of endothelial cell proliferation, which was stimulated when cultured on NO-releasing hydrogels that contained the cell adhesion peptide sequence REDV. The last bar represents a statistical variance of $p<0.02$ versus either REDV or DETA-NO hydrogels alone.

Hydrogels containing the cell adhesive ligand REDV were also prepared. Synthesis of acryloyl-PEG-REDV was identical to the synthesis of acryloyl-PEG-RGDS except that the concentration of REDV in the hydrogels was 14 μmol/ml and the concentration of RGDS was 1.4 μmol/ml. Endothelial cell seeding experiments were also identical. FIG. 14 shows the average cell number data for acryloyl-PEG-REDV.

EXAMPLE 12

NO-Producing PEG Derivatives Combined With PEG-Diacrylate

The monoacrylate NO-producing PEG derivatives have been combined with PEG-diacrylate to allow crosslinking into hydrogels. Biodegradable PEG-diacrylate derivatives, such as copolymers with α-hydroxy acids (Sawhney A S, Pathak C P, Hubbell J A. Bioerodible hydrogels based on photopolymerized poly(ethylene glycol)-co-poly(alpha-hydroxy acid) diacrylate macromers. *Macromol* 1993; 26: 581-587) or proteolytically degradable peptides (West J L, Hubbell J A. Polymeric biomaterials with degradation sites for proteases, involved in cell migration. *Macromol* 1999; 32: 241-244) could be substituted for PEG-diacrylate to create biodegradable, NO-producing hydrogels. This allows separate determination of NO production kinetics and biodegradation characteristics. Flexibility in the duration of NO release may also prove useful in the extension of this therapy to applications other than thrombosis and restenosis.

Example 13

Evaluation of Hydrogels for Enhancement of Wound Healing

In vitro Evaluation of Effects of PVA-NO on Fibroblast Viability and Proliferation Human dermal fibroblasts (HDFs, passage 5-11, Clonetics) were cultured in Dulbecco's Modified Eagle Medium supplemented with 10% FBS, 2 mM L-glutamnine, 500 units penicillin, and 100 mg/L streptomycin, at 37° C. in a 5% $CO_2$ environment. The effects of NO release from PVA-NO hydrogels on the viability and growth of HDFs were investigated in in vitro studies. HDFs were seeded at 8000 cells/$cm^2$ in 24-well tissue culture polystyrene plates. NO-releasing hydrogels containing 0.1 μmol to 5 μmol of the NO donor(0.1 mM to 5 mM NO donor in 1 ml cell culture media) were polymerized and suspended in the cell culture media in transwell inserts 24 hours following cell seeding. The hydrogels release NO over a period of approximately two days. Viability after 4 days of culture was assessed using trypan blue dye exclusion. After 4 days of culture, the cells were counted using a Coulter Counter to assess the effect of NO release on cell proliferation.

In vitro Evaluation of the Effects of PVA-NO on Extracellular Matrix Production

Extracellular matrix (ECM) production was assessed in fibroblast culture through incorporation of $^3$H-glycine into glycoprotein, elastin, and collagen portions of the ECM as determined by sequential enzyme digestion (TEC assay; Scott-Burden T, Resink T, Bürgin M, Bühler F. Extracellular matrix: Differential influence on growth and biosynthesis patterns of vascular smooth muscle cells from SHR and WKY rats. *J Cell Physiol* 1989; 141: 267-274). HDFs were seeded at 8000 cells/$cm^2$ in 24-well tissue culture polystyrene plates, and PVA-NO hydrogels were formed in transwell inserts and added to the cell culture media 24 hours following cell seeding. The media was supplemented with 1 μCi/ml $^3$H-glycine at this time. The same procedure was followed for cells intended for counting, except that the media was not supplemented with $^3$H-glycine. Two days following the addition of the hydrogels, the cells in non-radioactive wells were trypsinized and counted on a Coulter Counter. The cells in the remaining wells were lysed in a solution of 25 mM ammonium hydroxide for 30 minutes, and the plate was then dehydrated. A sequential digestion of extracellular matrix was performed in order to digest glycoproteins, elastin, and collagen. Radioactivity in samples from each digestion step was determined by scintigraphy (Minaxiβ Tri-Carb 4000, Packard Instrument Co., Meridien, Conn.).

In vivo Evaluation of PVA-NO Hydrogels for Enhancement of Wound Healing

The animal model used for in vivo testing of the PVA-NO hydrogels was a full thickness wound (1.5 cm diameter) in the dorsal skin of genetically diabetic (C57BLK/J-m+/+/$Lepr^{db}$) female mice, 8 weeks of age (Jackson Labs., Bar Harbor, Minn.). A total of 21 mice were used with equal numbers being assigned to each of 3 groups (2 test groups and 1 control group). Using the results from in vitro studies as well as data from the literature, the doses of NO selected for in vivo studies were set at 0.5 and 5 mM. These concentrations correspond to a total of 0.5 μmol and 5 μmol, respectively, of NO released from the hydrogels over a period of approximately 30 hours. Test groups had either 0.5 mM or 5 mM hydrogels applied and control group were dressed with PVA hydrogel without NO added. At time=0 days, a full thickness, 1.5 cm diameter wound was created. Mice were anesthetized by isoflurane inhalation and the dorsal skin was prepared for surgery using Betadine and 70% isopropanol. A full thickness, 1.5 cm diameter wound was created by surgical excision of epidermal and dermal layers. A circular piece of sterile PVA-NO or control hydrogel was cut to match the size of the wounds using a sterile circular cork borer, and applied to the wound. The wounds were covered with a transparent semi-occlusive secondary dressing (Tegaderm, 3M), adhered to the area surrounding the wound using tincture of Benzoin.

Every 2 to 3 days following surgery, wounds were redressed while the mice were under isoflurane inhalation anesthesia. The secondary dressing and the hydrogel were removed and the wounds were flushed with sterile saline to remove debris and to clean the wound area. A digital planimetric image of the wound was recorded using a Pixera video camera. A calibration scale was recorded with each image. Once photographed, fresh dressings were placed on the wounds, and the wounds were covered again with fresh Tegaderm dressings.

Wound area was assessed by image analysis using ImagePro Plus 3.0 image analysis software. Using the acquired images and this software, the perimeter of the wound was defined and measured, and the wound areas determined. Means and standard deviations of wound perimeters and areas at each time point were calculated.

One animal from each group was sacrificed at each time point of 8, 15 and 22 days and the final 4 animals from each group were sacrificed at 29 days. Histology was conducted on one animal from each group at each time point. Tissue surrounding and underlying the wound was sampled from these mice at the time of sacrifice and was fixed in Streck tissue fixative (Zinc-formalin), and embedded in paraffin for histological sectioning. Sections from each wound were stained with Hematoxylin and Eosin and with Masson's Trichrome stains. Granulation tissue thickness was measured at days 8 and 15 and collagen layer thickness was measured in sections from the final time point (29 days). Tissue thickness was measured using ImagePro Plus 3.0 image analysis software on images captured using an Olympus BX50WI microscope and SONY DKC 5000 camera.

Control of bias was achieved by assigning a color code to each of the test groups and the control group. Investigators were blinded to the identity of each of the groups and the test and control hydrogels have a similar appearance. All animal experimentation was conducted under appropriate procedures approved by the University of Medicine and Dentistry of New Jersey animal care and use review boards.

Characterization of Release Kinetics

As shown previously, release of NO from PVA-NO hydrogels was observed over a period of 48 hours at pH 7.4, as determined by the Griess assay. A slightly acidic pH is often observed in the wound environment, causing us to also evaluate NO release from these hydrogels at pH 6. No inhibition of NO release was observed when hydrogels were exposed to slightly acidic conditions. Hydrogels may be tailored to obtain a range of NO concentrations by blending with unreacted animated PVA prior to polymerization, allowing easy tailoring of the NO dosage. Control hydrogels for release kinetics studies consisted of animated PVA which had not been exposed to NO, as well as unmodified PVA (no amine groups) which had been exposed to NO, but did not contain any reactive groups with which to form NO donors. No significant NO release was observed with either control group.

In vitro Evaluation of Effects of PVA-NO on Cell Liability, Proliferation, and ECM Synthesis Exposure of HDFs to range of concentrations of PVA-NO hydrogels did not affect cell viability, as measured by trypan blue exclusion. Cells in all conditions remained >90% viable, even at the highest NO concentration of 5 mM. There was also no change in cell proliferation, as measured by cell counts (FIG. 14).

Figure 15:
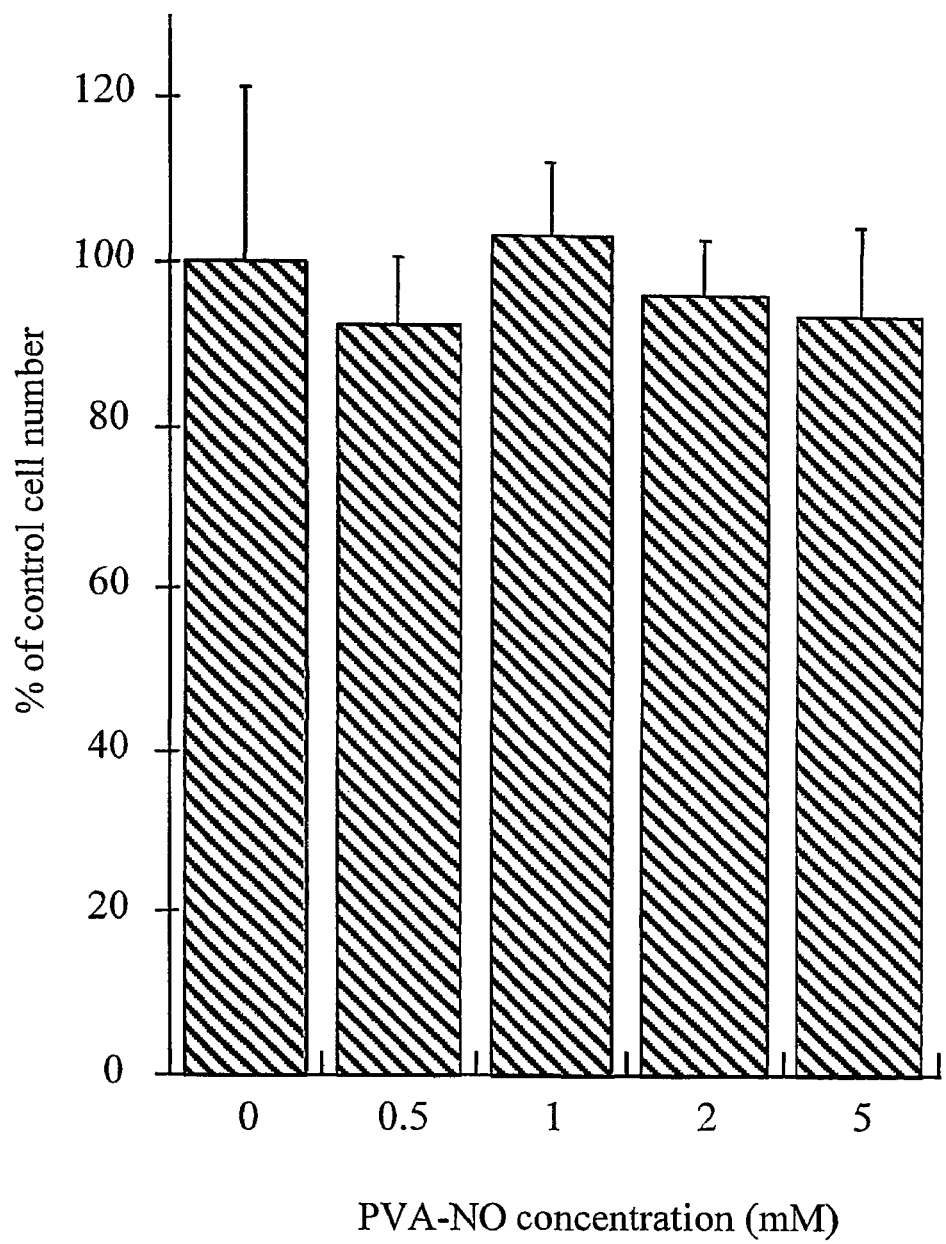
FIG. 15 is a graph of the proliferation of HDFs cultured in the presence of NO-releasing PVA hydrogels by cell counts. No significant changes in proliferation were observed with exposure to PVA-NO materials.

Analysis of ECM synthesis by HDFs cultured in the presence of PVA-NO hydrogels for two days indicated increased collagen production with increasing NO concentration (FIG. 15A; $p<0.01$). There was also a slight increase in overall matrix production by cells exposed to 5 MM PVA-NO, although this difference was not significant (FIG. 15B).

In vivo Evaluation of PVA-NO Hydrogels for Enhancement of Wound Healing

Figure 16A:
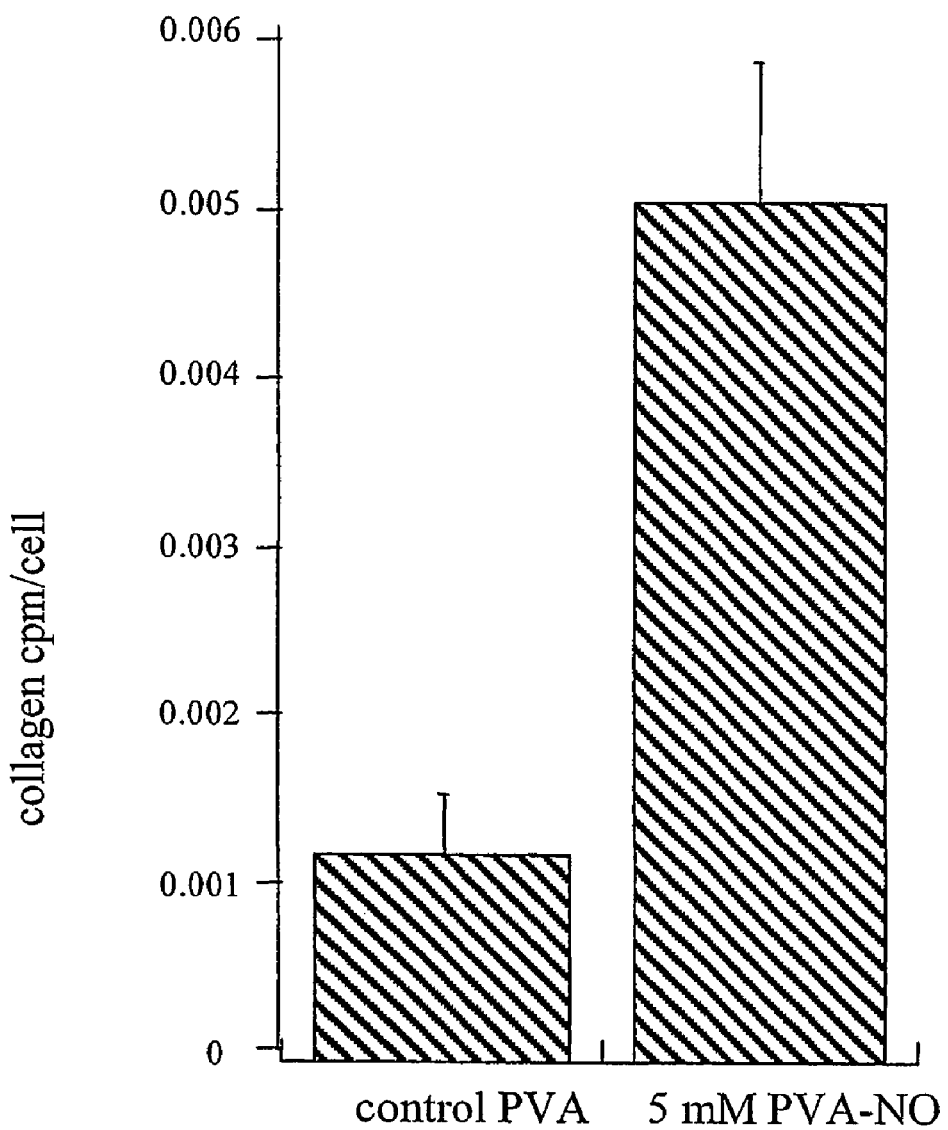
FIGS. 16A and 16B are graphs of the matrix production by fibroblasts cultured in the presence of NO-releasing PVA hydrogels. 16A shows the release of NO from PVA hydrogels increased the production of collagen by HDFs ($p<0.01$ versus control) while 16B shows only slightly increased total matrix produced per cell ($p>0.05$).
Figure 16B:
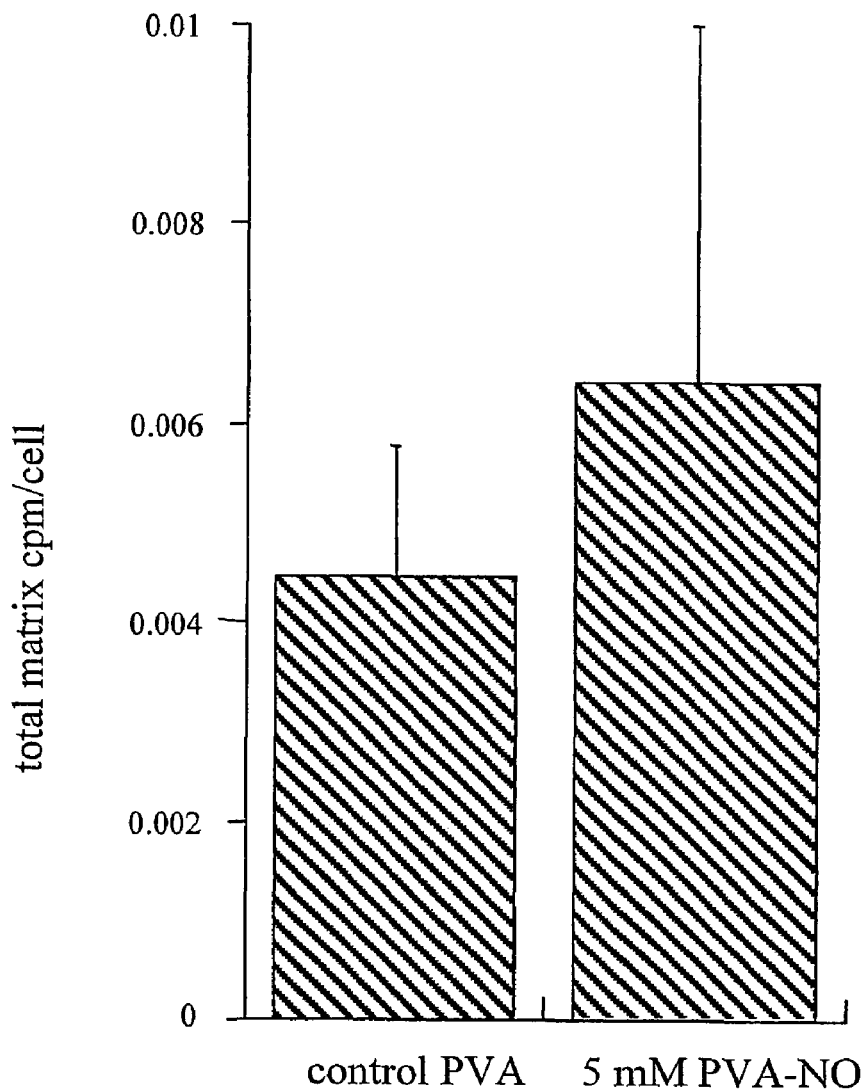

Wound closure first occurred by day 15 in one of 6 remaining animals in the control group. At day 22, ⅖ animals remaining in both the control and the 5 mM PVA-NO group had closed wounds whereas none in the 0.5 mM were closed. By day 27, of four animals remaining in each group, one in the 0.5 mM PVA-NO group, two in the control group and three in the 5 mM group had closed, epithelialized wounds. FIGS. 16A and 16B show the wound area and perimeter over time. Representative digital images of the wounds at days 10, 17, and 27 were also taken. Images of the wounds were captured every 2-3 days to quantify wound area and perimeter through image processing software. Day 27 was the endpoint of the wound healing study, with animals having closed, epithelialized wounds. Wound area and perimeter were similar in test and control groups.

Figure 17A:
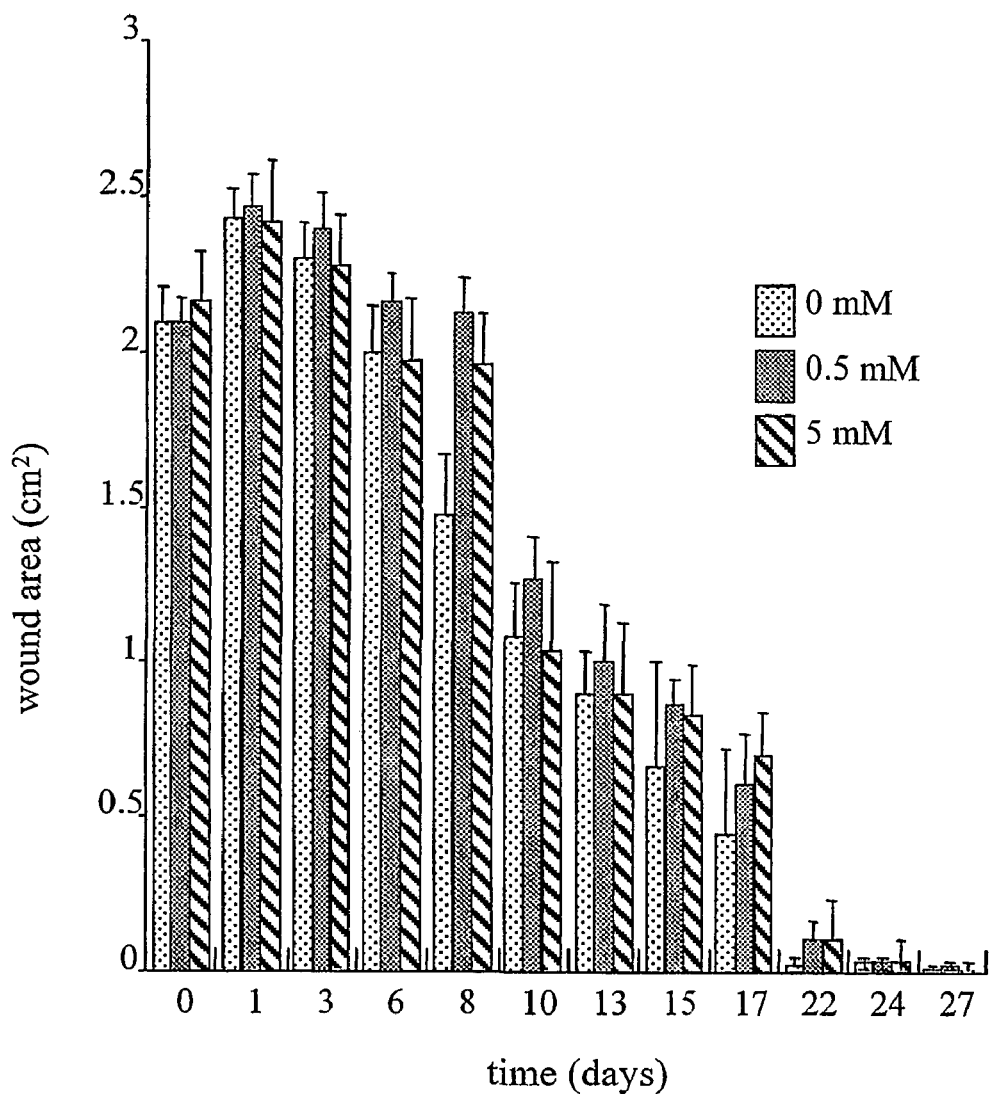
FIGS. 17A and 17B are graphs comparing wound area and perimeter over time. At the time of each dressing change, pictures of the wounds were taken to assess wound area (17A) and wound perimeter (17B) using image analysis software. No difference in wound area or perimeter was observed between control and NO hydrogel treatment groups.
Figure 17B:
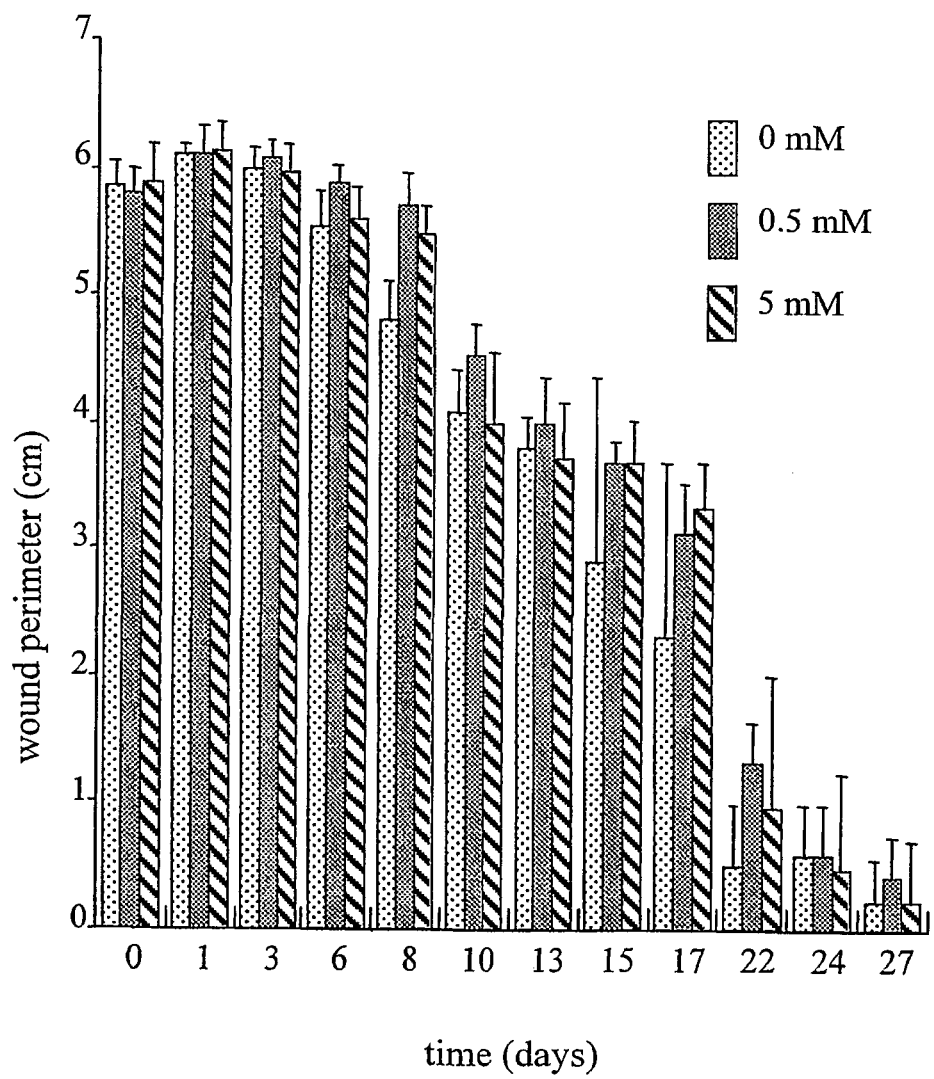

Granulation tissue, characterized by proliferating fibroblasts and newly formed microvasculature, was present in the open wound at days 8 and 15 in all groups. FIG. 17 shows a graph of the granulation tissue thickness comparing the test and control groups. The results reflect the mean thickness and standard deviation of 3 measurements taken on each of two serial sections (total of 6 measurements) within the region of the open wound. The three measurements were at a central point and 0.5 mm on either side of this point. Granulation tissue tended to be thicker with increasing NO concentration, however this difference was not statistically significant. Representative histological sections of granulation tissue formation at days 8 and 15 in the control group and the 5 mM PVA-NO group. Granulation tissue thickness was assessed through analysis of histological sections stained with hematoxylin and eosin. Representative sections were taken for treatment with a) control hydrogels and b) 5 mM PVA-NO hydrogels at day 8, as well as treatment with c) control hydrogels and d) 5 mM PVA-NO hydrogels at day 15. Increased granulation tissue thickness was observed in wounds treated with NO-releasing hydrogels compared to controls.

Figure 18:
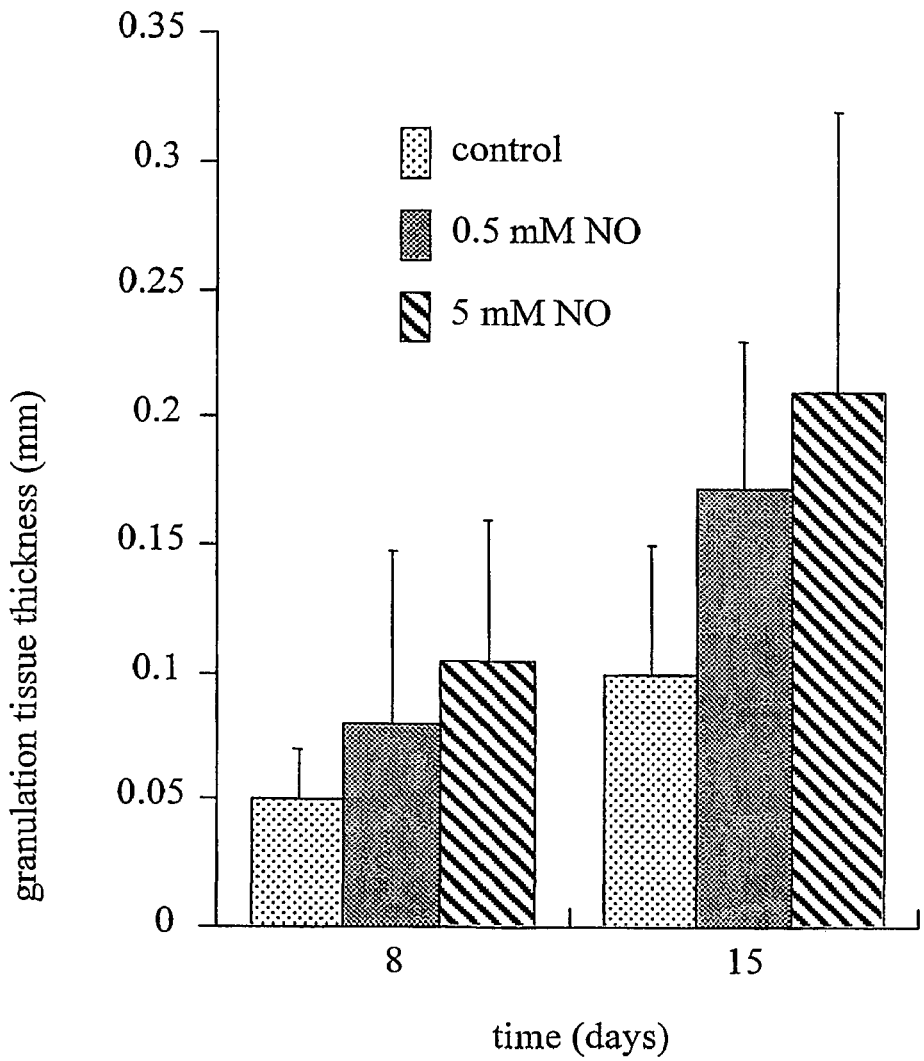
FIG. 18 is a graph of the granulation tissue thickness of wounds by examination of histological sections from wounds treated with PVA or PVA-NO hydrogels. A trend of increasing granulation tissue thickness with increasing NO concentration was observed.
Figure 19:
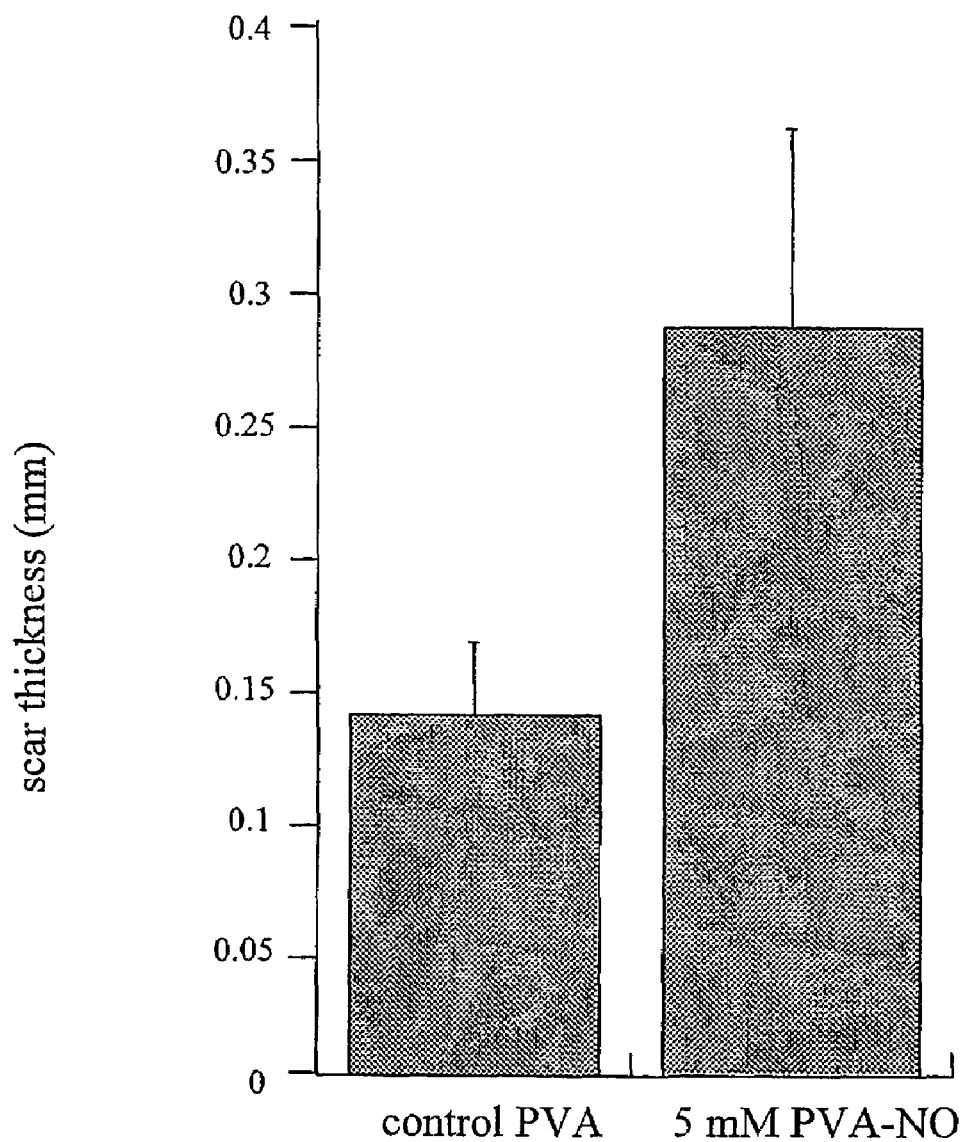
FIG. 19 is a graph reflecting wound collagen synthesis. Histological sections from animals at day 29 revealed that wound collagen synthesis was significantly increased through treatment with NO-releasing hydrogels. The second bar represents a statistical variance of $p<0.001$ versus control.

Collagen deposition was assessed in histological sections stained with Masson's Trichrome at day 29, after wounds were completely closed and epithelialized. This was measured in a similar way to granulation tissue at a central point and 2 points on either side 0.5 mm of the central point. Measurements were conducted on 4 sections from each animal. FIG. 18 shows a graph of the collagen tissue thickness (mean±SD) in the control and 5 mM test group. The collagen was significantly thicker in the NO treated group ($p<0.001$).

Modifications and variations of the methods and materials described herein will be obvious to those skilled in the art from the foregoing detailed description and accompanying figures. These methods and materials are intended to be encompassed by the following claims.

The invention claimed is:

1. A method of treating a disorder or condition with NO comprising administering to an individual in need thereof a biocompatible, polymerizable, macromer composition comprising at least one NO carrying region or NO modulating compound, wherein the NO or NO modulating compound is released from the macromer composition, wherein the macromer composition comprises a macromer having regions selected from the group consisting of a water soluble region, a cell adhesion ligand, and a polymerizable region.

2. The method of claim 1 wherein the macromer further comprises degradable regions.

3. The method of claim 1 for treatment of a disorder or condition selected from the group consisting of wound healing, restenosis, thrombosis, asthma, arthritis, and erectile dysfunction.

4. The method of claim 1 wherein the macromer is adhered to or coated onto tissue.

5. The method of claim 1 wherein the macromer is adhered to or coated onto a medical device for facilitating the growth of endothelial cells onto the medical device.

6. The method of claim 5 wherein the medical device or implant is a vascular graft, catheter or stent.

7. The method of claim 6 wherein the medical device is a graft for use in performing dialysis.

8. The method of claim 1 wherein the cell adhesion ligand is RGD, RGDS or REDV.

* * * * *